United States Patent
Case et al.

(10) Patent No.: US 11,386,993 B2
(45) Date of Patent: *Jul. 12, 2022

(54) PLASMA COLLECTION WITH REMOTE PROGRAMMING

(71) Applicant: Fenwal, Inc., Lake Zurich, IL (US)

(72) Inventors: Brian C. Case, Lake Villa, IL (US); Lan T. Nguyen, Vernon Hills, IL (US); Amit J. Patel, Algonquin, IL (US); Samantha M. Planas, Wauconda, IL (US); Walter T. Watts, Lake Forest, IL (US); Kyungyoon Min, Kildeer, IL (US); Daniel R. Boggs, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/078,824

(22) Filed: Oct. 23, 2020

(65) Prior Publication Data

US 2021/0043316 A1    Feb. 11, 2021

Related U.S. Application Data

(63) Continuation-in-part of application No. PCT/US2019/033318, filed on May 21, 2019.

(Continued)

(51) Int. Cl.
*G16H 40/60* (2018.01)
*G16H 10/60* (2018.01)
(Continued)

(52) U.S. Cl.
CPC .............. *G16H 40/60* (2018.01); *A61B 34/10* (2016.02); *A61M 1/34* (2013.01); *A61M 1/3403* (2014.02);
(Continued)

(58) Field of Classification Search
CPC ........ G16H 40/60; G16H 10/60; A61B 34/10; A61M 1/34; A61M 1/3403;
(Continued)

(56) References Cited

U.S. PATENT DOCUMENTS

| 5,112,298 A | 5/1992 | Prince et al. |
| 5,178,603 A | 1/1993 | Prince |

(Continued)

FOREIGN PATENT DOCUMENTS

| CN | 204446748 U | 7/2015 |
| CN | 104800905 B | 12/2016 |

(Continued)

OTHER PUBLICATIONS

Trima Accel Automated Blood Clot system Service Manual, 3-83 (Year: 2015).*

(Continued)

*Primary Examiner* — Nabil H Syed
*Assistant Examiner* — Cal J Eustaquio
(74) *Attorney, Agent, or Firm* — Becker Patent Law, LLC

(57) ABSTRACT

A system and method for collecting plasma includes drawing whole blood from a donor, combining anticoagulant with the whole blood from the donor, separating the whole blood into a plasma product and a second blood component and sending the plasma product to a collection container. A controller receives parameters over a network from a remote computer, receives a user input to confirm the a parameter and/or procedure, determines a target volume for plasma product and/or raw plasma based on the parameters and, in response to confirming the donor, controls the system to collect the plasma using draw and return phases.

22 Claims, 15 Drawing Sheets

| DONOR WEIGHT | PLASMA VOLUME OR WEIGHT | COLLECTION VOLUME |
|---|---|---|
| 110-149 lbs. | 625 mL (640 g) | 690 mL (705 g) |
| 150-174 lbs. | 750 mL (770 g) | 825 mL (845 g) |
| 175 lbs. & UP | 800 mL (820 g) | 880 mL (900 g) |

Related U.S. Application Data

(60) Provisional application No. 62/846,400, filed on May 10, 2019, provisional application No. 62/752,480, filed on Oct. 30, 2018, provisional application No. 62/674,144, filed on May 21, 2018.

(51) Int. Cl.
| | |
|---|---|
| *A61M 1/34* | (2006.01) |
| *A61B 34/10* | (2016.01) |
| *G06F 21/31* | (2013.01) |
| *G08B 3/10* | (2006.01) |
| *G08B 5/22* | (2006.01) |

(52) U.S. Cl.
CPC .............. *G06F 21/31* (2013.01); *G08B 3/10* (2013.01); *G08B 5/22* (2013.01); *G16H 10/60* (2018.01); *H05K 999/99* (2013.01); *A61M 2205/33* (2013.01); *A61M 2205/3334* (2013.01)

(58) Field of Classification Search
CPC ...... A61M 2205/33; G06F 21/31; G08B 3/10; G08B 5/22; H05K 999/99
See application file for complete search history.

(56) References Cited

U.S. PATENT DOCUMENTS

| | | | |
|---|---|---|---|
| 5,496,265 A | 3/1996 | Langley et al. | |
| 5,681,273 A | 10/1997 | Brown | |
| 5,686,696 A | 11/1997 | Baker, Jr. et al. | |
| 6,007,725 A | 12/1999 | Brown | |
| 6,080,322 A | 6/2000 | Deniega et al. | |
| 6,183,651 B1 | 2/2001 | Brown et al. | |
| 6,200,287 B1 | 3/2001 | Keller et al. | |
| 6,207,063 B1 | 3/2001 | Brown | |
| 6,251,284 B1 | 6/2001 | Bischoff et al. | |
| 6,284,142 B1 | 9/2001 | Muller | |
| 6,325,775 B1* | 12/2001 | Thom | A61M 1/3693 604/6.02 |
| 6,348,156 B1 | 2/2002 | Vishnoi et al. | |
| 6,471,855 B1 | 10/2002 | Odak | |
| 6,641,552 B1 | 11/2003 | Kingsley et al. | |
| 6,695,806 B2 | 2/2004 | Gelfand et al. | |
| 6,730,054 B2 | 5/2004 | Pierce et al. | |
| 6,983,884 B2 | 1/2006 | Auchlinleck | |
| 7,050,611 B2 | 5/2006 | Bodicker et al. | |
| 7,186,231 B2 | 3/2007 | Takagi et al. | |
| 7,282,154 B2 | 10/2007 | Muller | |
| 7,354,415 B2 | 4/2008 | Bainbridge et al. | |
| 8,204,694 B2 | 6/2012 | Hauck et al. | |
| 8,287,818 B2 | 10/2012 | Kantrowitz et al. | |
| 8,405,508 B2 | 3/2013 | Burke | |
| 8,746,547 B2 | 6/2014 | Mollstam et al. | |
| 8,840,790 B2 | 9/2014 | Wegener et al. | |
| 9,011,359 B2 | 4/2015 | Wegener et al. | |
| 9,095,665 B2 | 8/2015 | Pagès et al. | |
| 9,302,042 B2 | 4/2016 | Pagès et al. | |
| 9,364,600 B2 | 6/2016 | Pagès et al. | |
| 2002/0151804 A1 | 10/2002 | O'Mahony et al. | |
| 2003/0125017 A1 | 7/2003 | Greene et al. | |
| 2003/0125881 A1 | 7/2003 | Ryan | |
| 2003/0140928 A1* | 7/2003 | Bui | G16H 20/13 128/898 |
| 2004/0183683 A1 | 9/2004 | Funahashi | |
| 2004/0199098 A1 | 10/2004 | Pierce et al. | |
| 2005/0228238 A1 | 10/2005 | Monitzer | |
| 2005/0258238 A1* | 11/2005 | Chapman | G07C 9/25 235/380 |
| 2006/0093190 A1 | 5/2006 | Cheng et al. | |
| 2006/0226086 A1 | 10/2006 | Robinson et al. | |
| 2007/0018832 A1 | 1/2007 | Biegel | |
| 2007/0067452 A1 | 3/2007 | Fung | |
| 2007/0138069 A1 | 6/2007 | Roncadi | |
| 2007/0258626 A1 | 11/2007 | Reiner | |
| 2007/0268130 A1 | 11/2007 | Yee | |
| 2009/0215602 A1 | 8/2009 | Min et al. | |
| 2009/0275808 A1 | 11/2009 | Dimaio et al. | |
| 2010/0100392 A1* | 4/2010 | Rothman | G16H 15/00 705/2 |
| 2012/0010062 A1* | 1/2012 | Fletcher | A61M 1/38 494/10 |
| 2012/0053501 A1* | 3/2012 | Brown | H05K 999/99 604/6.07 |
| 2012/0175313 A1 | 7/2012 | Barry, Jr. et al. | |
| 2015/0367063 A1* | 12/2015 | Kimura | A61M 1/3693 494/10 |
| 2018/0344910 A1 | 12/2018 | Ragusa | |
| 2018/0344921 A1 | 12/2018 | Ragusa | |

FOREIGN PATENT DOCUMENTS

| | | |
|---|---|---|
| JP | 2002-282352 A | 10/2002 |
| JP | 3936132 B2 | 6/2007 |
| RU | 2252788 C1 | 5/2005 |
| WO | WO2018222441 A1 | 12/2018 |

OTHER PUBLICATIONS

Russian Patent Office, Russian Search Report for RU2252788C1 with English translation dated Jun. 2, 2021 (4 pages).

Notice of Reasons of Refusal with English translation, counterpart Japanese application 2020-202093 dated Jun. 15, 2021 (8 pages).

International Search Report and Written Opinion, counterpart International Appl. No. PCT/US2019/033318 (dated Aug. 21, 2019) (14 pages).

Pearson, T.C. et al., Interpretation of measured red cell mass and plasma volume in adults: Expert Panel on Radionuclides of the International Council for Standardization of Haematology, British Journal of Haematology, 1995, 89, pp. 748-756 (9 pages).

Compliance Program Guidance Manual, Chapter 42—Blood and Blood Components, Inspection of Source Plasma Establishments, Brokers,Testing Laboratories, and Contractors—7342.002, Completion Date: Jan. 31, 2019, (63 pages).

Director, Center for Biologics Evaluation and Research, Volume Limits for Automated Collection of Source Plasma, Nov. 4, 1992 (3 pages).

Examination report No. 1 for standard patent application for Australian patent No. 2019274489 dated Nov. 16, 2020 (4 pages).

Examination report No. 1 for standard patent application for Australian patent No. 2020267188 dated Nov. 25, 2020 (7 pages).

Notice of Reasons of Refusal with English translation, counterpart Japanese application 2020-557304 dated May 11, 2021 (8 pages).

Notice of Preliminary Rejection with English translation for Korean Patent Application No. 10-2020-7033175 dated Mar. 22, 2021 (13 pages).

Notice of Preliminary Rejection with English translation for Korean Patent Application No. 10-2020-7033247 dated Mar. 22, 2021 (31 pages).

Response to Examiner's Report for Australian Patent Application 2019274489 dated Mar. 16, 2021 (12 pages) (12 pages).

Response to Examiner's Report for Australian Patent Application 2020267188 dated Mar. 16, 2021 (12 pages) (20 pages).

Response to Notice of Preliminary Rejection with English translation for Korean Patent Application No. 10-2020-7033175 dated May 24, 2021 (33 pages).

Amendment to the application with English translation for Korean Patent Application No. 10-2020-7033175 dated May 24, 2021 (11 pages).

Response to Notice of Preliminary Rejection with English translation for Korean Patent Application No. 10-2020-7033247 dated May 24, 2021 (42 pages).

Amendment to the application with English translation for Korean Patent Application No. 10-2020-7033247 dated May 24, 2021 (40 pages).

Amendment and Reply in U.S. Appl. No. 16/739,441 dated Apr. 5, 2022, 13 pages.

(56) References Cited

OTHER PUBLICATIONS

Amendment in U.S. Appl. No. 17/306,099 dated Apr. 5, 2022, 18 pages.
Request for Examination in EP21168049 dated Mar. 29, 2022, 12 pages.
Examiner Requisition in Canada App. 3,099,428 dated Mar. 28, 2022, 4 pages.
Notice for Reasons for Refusal in Japan App. 2020-202093 dated Jan. 11, 2022, 3 pages.
Notice of Allowance in U.S. Appl. No. 17/386,992 dated Feb. 9, 2022, 8 pages.
U.S. Appl. No. 17/675,824, filed Feb. 18, 2022.
U.S. Appl. No. 17/306,099, filed May 3, 2021.
U.S. Appl. No. 16/739,441, filed Jan. 10, 2020.
PCT/US21/33835, filed May 24, 2021.
Extended European Search Report, counterpart EP Application No. 21168049.1 (Aug. 17, 2021) (8 pages).

* cited by examiner

| DONOR WEIGHT | PLASMA VOLUME OR WEIGHT | COLLECTION VOLUME |
|---|---|---|
| 110-149 lbs. | 625 mL (640 g) | 690 mL (705 g) |
| 150-174 lbs. | 750 mL (770 g) | 825 mL (845 g) |
| 175 lbs. & UP | 800 mL (820 g) | 880 mL (900 g) |

VOLUME OF RAW PLASMA IN PLASMA PRODUCT (mL) FOR A 1:16 AC RATIO

| DONOR WEIGHT LBS | PLASMA PRODUCT VOLUME (mL) | DONOR HEMATOCRIT (%) | | | | | | | | | | |
|---|---|---|---|---|---|---|---|---|---|---|---|---|
| | | 36 | 38 | 40 | 42 | 44 | 46 | 48 | 50 | 52 | 54 | 56 |
| 110-149 | 690 | 629 | 627 | 625 | 623 | 621 | 618 | 616 | 613 | 611 | 607 | 604 |
| 150-174 | 825 | 752 | 749 | 747 | 745 | 742 | 739 | 736 | 733 | 730 | 726 | 722 |
| 175 & up | 880 | 802 | 799 | 797 | 794 | 792 | 789 | 786 | 782 | 779 | 775 | 771 |

Fig. 8

UNCLAIMED RAW PLASMA (mL) FOR A 1:16 AC RATIO

| DONOR WEIGHT LBS | PLASMA PRODUCT VOLUME (mL) | DONOR HEMATOCRIT (%) | | | | | | | | | | |
|---|---|---|---|---|---|---|---|---|---|---|---|---|
| | | 36 | 38 | 40 | 42 | 44 | 46 | 48 | 50 | 52 | 54 | 56 |
| 110-149 | 690 | -4 | -2 | 0 | 2 | 4 | 7 | 9 | 12 | 14 | 18 | 21 |
| 150-174 | 825 | -2 | 1 | 3 | 5 | 8 | 11 | 14 | 17 | 20 | 24 | 28 |
| 175 & up | 880 | -2 | 1 | 3 | 6 | 8 | 11 | 14 | 18 | 21 | 25 | 29 |

Fig. 9

ALLOWED PLASMA PRODUCT VOLUME (mL) FOR A 1:16 AC RATIO

| DONOR WEIGHT LBS | DONOR HEMATOCRIT (%) | | | | | | | | | | | |
|---|---|---|---|---|---|---|---|---|---|---|---|---|
| | RAW VOLUME | 36 | 38 | 40 | 42 | 44 | 46 | 48 | 50 | 52 | 54 | 56 |
| 110-149 | 625 | 686 | 688 | 690 | 692 | 695 | 697 | 700 | 703 | 706 | 710 | 714 |
| 150-174 | 750 | 823 | 826 | 828 | 831 | 834 | 837 | 840 | 844 | 848 | 852 | 857 |
| 175 & up | 800 | 878 | 881 | 883 | 886 | 889 | 893 | 896 | 900 | 904 | 909 | 914 |

| INPUTS | |
|---|---|
| DONOR WEIGHT (lbs) | 190 |
| STARTING DONOR HCT (%) | 44 |
| TARGET RAW PLASMA VOL (mL) | 800 |
| BLOOD VOLUME (mL/kg) | 62.5 |
| PLASMA REPLACEMENT RATE (mL/min) | 0 |
| DONOR WEIGHT (kg) | 86.4 |
| RBC VOLUME (mL) | 2375 |
| PLASMA VOLUME (mL) | 3023 |
| DRAW VOLUME (mL WB) | 500 |
| AC RATIO (1:xx) | 16 |
| EFFICIENCY | 70% |

*Fig. 10*

| DESCRIPTION | DONOR RBC VOL (mL) | DONOR PLASMA VOL (mL) | DONOR HCT (%) | AC DRAWN (mL) | RBC DRAWN (mL) | RAW PLASMA DRAWN (mL) |
|---|---|---|---|---|---|---|
| CYCLE 1 START | 2375 | 3023 | 44.0% | | | |
| CYCLE 1 DRAW END | 2155 | 2743 | 44.0% | 31 | 220 | 280 |
| CYCLE 1 RETURN END | 2375 | 2836 | 45.6% | | | |
| CYCLE 2 DRAW END | 2147 | 2564 | 45.6% | 31 | 228 | 272 |
| CYCLE 2 RETURN END | 2375 | 2655 | 47.2% | | | |
| CYCLE 3 DRAW END | 2139 | 2391 | 47.2% | 31 | 236 | 264 |
| CYCLE 3 RETURN END | 2375 | 2480 | 48.9% | | | |
| CYCLE 4 DRAW END | 2130 | 2224 | 48.9% | 31 | 245 | 255 |
| CYCLE 4 RETURN END | 2375 | 2310 | 50.7% | | | |
| CYCLE 5 DRAW END | 2301 | 2239 | 50.7% | 31 | 245 | 255 |
| CYCLE 5 RETURN END | 2375 | 2263 | 51.2% | | | |

Fig. 11a

| DESCRIPTION | RESERVOIR RBC VOL (mL) | RESERVOIR NON RBC VOL (mL) | COLLECTION VOL (mL) | COLLECTED PLASMA (mL) | COLLECTED RAW VOL (mL) | TARGET COLLECTION VOL (mL) |
|---|---|---|---|---|---|---|
| CYCLE 1 START | 0 | 0 | 0 | 0 | 0 | 889 |
| CYCLE 1 DRAW END | 220 | 93 | 218 | 196 | | |
| CYCLE 1 RETURN END | 0 | 0 | 218 | 196 | | 891 |
| CYCLE 2 DRAW END | 228 | 91 | 430 | 386 | | |
| CYCLE 2 RETURN END | 0 | 0 | 430 | 386 | | 893 |
| CYCLE 3 DRAW END | 236 | 89 | 637 | 571 | | |
| CYCLE 3 RETURN END | 0 | 0 | 637 | 571 | | 894 |
| CYCLE 4 DRAW END | 245 | 86 | 837 | 750 | | |
| CYCLE 4 RETURN END | 0 | 0 | 837 | 750 | | 894 |
| CYCLE 5 DRAW END | 74 | 24 | 894 | 800 | | |
| CYCLE 5 RETURN END | 0 | 0 | 894 | 800 | | 894 |

*Fig. 11b*

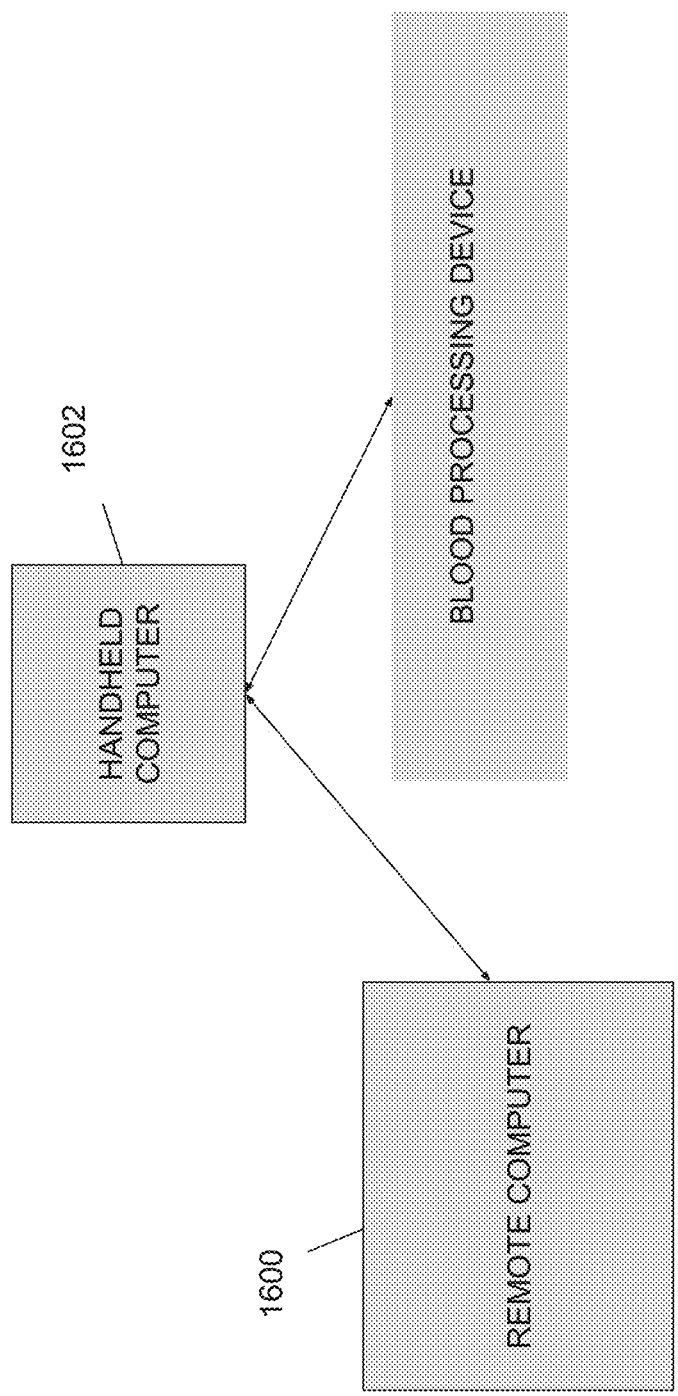

PLASMA COLLECTION WITH REMOTE PROGRAMMING

CROSS REFERENCE TO RELATED APPLICATIONS

This application is a continuation-in-part of International Application No. PCT/US2019/033318 filed May 21, 2019, which claims the benefit of U.S. Provisional Application Nos. 62/674,144 filed May 21, 2018, 62/752,480 filed Oct. 30, 2018 and 62/846,400 filed May 10, 2019, all of which are hereby incorporated by reference herein in their entireties.

This application is related to application Ser. No. 16/842,879, filed Apr. 8, 2020, application Ser. No. 16/545,962, filed Aug. 20, 2019, now U.S. Pat. No. 10,643,748, application Ser. No. 16/162,867, filed Oct. 17, 2018, now U.S. Pat. No. 10,431,334, application Ser. No. 15/836,227, filed Dec. 8, 2017, now U.S. Pat. No. 10,130,747, application Ser. No. 14/455,413 filed Aug. 8, 2014, now U.S. Pat. No. 9,867,922, and application Ser. No. 13/110,520 filed May 18, 2011, all of which are hereby incorporated by reference herein in their entireties.

BACKGROUND

The present application relates to systems and methods for performing plasmapheresis and, more particularly, to plasmapheresis systems and methods in which the volume of source or raw plasma product that may be collected from a particular donor is optimized. The present subject matter also relates to systems and methods for controlling the performance of a medical procedure on a subject.

Plasmapheresis is an apheresis procedure in which whole blood is withdrawn from a donor, the plasma separated from the cellular blood components (red blood cells, platelets and leukocytes) and retained, and the cellular blood components returned to the donor. The separation of the plasma from the cellular components is typically accomplished in an automated procedure by centrifugation or membrane filtration.

In automated plasmapheresis, whole blood is drawn from the donor, mixed at a specified ratio with anticoagulant ("AC"), and then separated into anticoagulated plasma and red blood cells and other cellular components. Once a target volume of anticoagulated plasma (or "plasma product") has been collected, as determined by a weigh scale associated with a plasma collection container, the withdrawal of whole blood from the donor ceases, and the red blood cells and other cellular components are returned to the donor. Often, the plasma product is collected in multiple collection and reinfusion cycles, until the total target volume of anticoagulated plasma has been collected. The anticoagulated plasma is used for later transfusion or further manufacturing.

Plasma that is collected to serve as a source material ("source plasma") for further manufacturing is collected from multiple donors and combined or pooled together for this purpose. The FDA issued guidelines for registered blood collection centers as to the volume of plasma that may be collected as source plasma during plasmapheresis in order to improve the consistency of procedures for manufacturing source plasma, and to minimize the opportunity for staff error. (FDA Memo: "Volume Limits-Automated Collection of Source Plasma (11/4/92)"). The FDA Memo noted inconsistencies due to the various types of anticoagulant solutions used, differing concentrations of the anticoagulant, and the range of anticoagulant to plasma ratios.

The FDA Memo set forth a simplified plasma volume nomogram, reproduced in the table shown in FIG. 1, in which the volume (or weight) of plasma that may be collected from a particular donor is limited to ensure donor safety and comfort. More specifically, the FDA nomogram limits the volume (or weight) of plasma based on the weight of the donor, and establishes the volume of anticoagulant that may be added to a 1:16 ratio of anticoagulant to anticoagulated blood, or 0.06 parts anticoagulant to 1 part anticoagulated blood, to arrive at a maximum collection volume for the total of the plasma plus the anticoagulant for a particular donor.

The simplified nomogram set forth in the FDA Memo has been the predominant method for determining plasma product collection volumes used by blood collection centers. Therefore, the plasmapheresis devices used at such centers are commonly programmed to collect a specified volume/weight of anticoagulated plasma (assuming a known density) in accordance with the maximum collection volume permitted by the FDA nomogram, with the anticoagulant being added to the whole blood at a 1:16 or 0.06 ratio.

One simplification made in the FDA nomogram is to exclude the consideration of donor hematocrit in determining the collection volume of the plasma product. However, the relative proportions of raw plasma and anticoagulant in the plasma product depends on the donor blood hematocrit and the ratio at which the AC is combined with the donor's whole blood. As a consequence, higher hematocrit donors reach the maximum collection volume set forth in the FDA nomogram before reaching the maximum (raw) plasma volume that may be safely collected from the donor. This represents an inefficiency for the plasma collection center, in that volume of raw plasma that is collected is less than the maximum amount possible.

Further, the amount of plasma that may be safely collected from a donor can depend on factors in addition to the donor's weight and hematocrit, such as the donor's height, sex and age, as these factors affect the donor's total blood volume (and volume of plasma).

Because the source plasma from multiple donors is combined, it is important to maximize the plasma volume that may be collected from each individual donor, as even small gains in volume collected from each individual donor, when added together, result in a meaningful increase in the total volume of the pooled plasma. If a plasmapheresis device were to be able to better target the raw plasma volume, more plasma proteins could be collected from each donor, improving the overall efficiency of the plasma collection center. Accordingly, by way of the present disclosure, systems and methods for optimizing the volume of plasma collected are provided which are consistent with donor safety and comfort.

The parameters under which an at least partially automated medical procedure is performed, including without limitation blood donations and apheresis, should correspond or be appropriate to the characteristics of the donor or patient upon which the procedure is being performed. For example, when performing a blood donation procedure, it may be advantageous for a number of parameters, such as the sex and weight of the donor or patient, to be taken into consideration. If the incorrect operational parameters are used, the procedure may be less efficient than it would otherwise be and/or in certain circumstances could possibly be harmful to the donor or patient. Accordingly, care should be taken that the operational parameters correspond to the unique characteristics of the donor or patient.

Information regarding the donor or patient may be present in a datasheet or written prescription and entered into the automated device or system via a user interface by the operator of the system (e.g., a nurse, doctor, or technician) at the beginning of the procedure. The operator confirms the settings of the system and the identity of the subject and then instructs the system to initiate the medical procedure. By relying on manual data entry, there is of course a risk of operator error, resulting in operational parameters which do not correspond to the unique characteristics of the donor or patient. Thus, systems and methods which reduce the risk of data entry errors would be advantageous.

SUMMARY

By way of the present disclosure, methods are provided for operating a plasmapheresis system to collect a volume of anticoagulated plasma (i.e., the plasma product) that insures that the total volume of raw plasma in the plasma product is the maximum that may be collected from a particular donor consistent with donor safety and comfort, whether as dictated by the donor's unique physical characteristics, as indicated by the FDA nomogram or by some other methodology.

In keeping with a first aspect of the disclosure, a method is provided for operating a plasmapheresis system to collect a plasma product volume that comprises the maximum allowable volume/weight of raw plasma in accordance with the limits set forth in the FDA nomogram based on the weight of the donor.

In order to collect the maximum volume/weight of raw plasma permitted by the FDA nomogram, a modified nomogram is provided that utilizes the donor's hematocrit to calculate a target volume/weight for a plasma product having the maximum volume of raw plasma permitted by the FDA nomogram. A calculated volume/weight of raw plasma is compared to the maximum volume/weight for the raw plasma permitted by the FDA nomogram. If the calculated volume/weight of raw plasma is less than the maximum permitted volume/weight, the volume/weight of the plasma product to be collected is adjusted upward from the maximum volume/weight permitted by the FDA nomogram for the plasma product by an amount equal to the difference plus the additional amount of anticoagulant that is added to process the additional volume/weight of plasma.

Thus, with the knowledge of the donor's hematocrit and the instrument's AC ratio, the volume of additional raw plasma that may be safely collected from the donor consistent with the limits set forth in the FDA nomogram is determined, and then the total volume/weight of plasma product to be collected based on the weight of the donor set forth in the FDA nomogram is adjusted accordingly.

Typically, plasmapheresis procedures involve sequential cycles of alternating phases, one in which whole blood is withdrawn from the donor and the plasma separated and collected, and the other in which the separated red blood cells and any other non-RBC cellular components are returned to the donor. The donor's hematocrit will change during the course of the plasmapheresis procedure, thus affecting the amount of anticoagulant in the plasma product collected from one cycle to the next.

Consequently, in the first aspect of the disclosure, before the commencement of the subsequent extraction/separation phase, a new hematocrit value for the donor is determined, and the target volume/weight of plasma product for the procedure is recalculated before the commencement of each extraction/separation phase to ensure that the maximum amount of raw plasma permitted by the FDA nomogram is collected.

In keeping with a second aspect, a further method for collecting a volume of plasma during an apheresis procedure is provided. The steps of the method comprise: determining a total whole blood volume $V_b$ for the donor; determining a volume of raw plasma ($V_{RP}$) that may be collected from the donor based on $V_b$; determining a target volume of plasma product ($V_{RP}$) to be collected, wherein $V_{PP}$ is equal to the volume of raw plasma ($V_{RP}$) to be collected plus a volume of anticoagulant ($V_{AC}$) that is added to the $V_{RP}$ during the apheresis procedure, such that $V_{PP}=V_{RP}*K$, where $K=(ACR*(1-Hct/100)+1)/(ACR*(1-Hct/100))$, based on an anticoagulant ratio (ACR, defined as the ratio of donor blood volume to anticoagulant volume for donor blood having no anticoagulant) established for the procedure and a Hct of the donor; withdrawing whole blood from the donor; adding anticoagulant to the whole blood in an amount consistent with the ACR; separating plasma product from the whole blood; and transferring the plasma product to a collection container until the volume of plasma product in the collection container reaches $V_{PP}$. Because the plasmapheresis procedure comprises multiple extraction/separation and return phases, the $V_{PP}$ for the procedure is recalculated before each extraction/separation phase is commenced, based on a value for the hematocrit of the donor determined prior to the start of each draw phase, and the target volume for the plasma product adjusted accordingly. Alternatively, $V_{RP}$ may be determined based on a calculated value for the donor's total plasma volume, based on $V_b$ and the donor's hematocrit.

In a third aspect, a method for determining a volume of plasma product ($V_{PP}$) that may be collected during an apheresis procedure is provided, wherein $V_{PP}$ is equal to a volume of raw plasma ($V_{RP}$) that may be collected plus a volume of anticoagulant ($V_{AC}$) that is added to the $V_{RP}$ during the apheresis procedure. The steps of the method comprise: determining a weight ($W_{kg}$) and sex (M or F) of the donor, determining a hematocrit (Hct) for the donor; determining the volume of raw plasma ($V_{RP}$) that may be collected based on the weight ($W_{kg}$) and sex (M or F) of the donor; determining a ratio K between the $V_{PP}$ and the $V_{RP}$, such that $K=V_{PP}/VR_{RP}$, based on an anticoagulant ratio (ACR) and the Hct of the donor; determining $V_{PP}$, such that $V_{PP}=V_{RP}*K$. Further, $K=(ACR*(1-Hct/100)+1)/(ACR*(1-Hct/100))$. After $V_{PP}$ is determined, whole blood is withdrawn from the donor; anticoagulant is added to the whole blood in an amount consistent with the ACR; plasma product is separated from the whole blood; and plasma product is transferred to a collection container. After a desired amount of whole blood has been withdrawn from the donor, the red blood cells are returned to the donor. Then, the Hct of the donor and $V_{PP}$ are determined prior to each draw phase.

In a related aspect, the draw and separation steps are repeated until the volume of plasma product in the collection container reaches $V_{PP}$.

In a related aspect, the donor's hematocrit subsequent to the first collection phase may be calculated by a volume balance, assuming that the donor's quantity of red blood cells is the same at the start of each draw cycle, while the total volume of blood decreases from one cycle to the next in an amount equal to the amount of raw plasma collected. Alternatively, the donor's hematocrit at the start of each draw cycle can be measured by an optical or other sensor.

In a further aspect, the volume of raw plasma that may be collected from a particular donor may be determined by any one of several different means. Such means include, e.g., the FDA nomogram, taking into account only the donor's weight; a modified FDA nomogram, further taking into account the donor's hematocrit, and taking a fraction of a total blood volume or total plasma volume calculated for a particular donor. The total blood volume or total plasma volume may be determined using, for example, Nadler's equations, Gilcher's Rule of Five, tables provided by the International Council for Standardization in Haematology (ICSH), or any other generally accepted method using the donor's height, weight, sex and age, consistent with the safety and comfort of the donor.

In a fourth aspect, an automated system for separating plasma from whole blood is provided that comprises a reusable hardware component and a disposable kit. The disposable kit further comprises: i) a separator for separating whole blood into a plasma fraction and a concentrated cell fraction, the separator having an input having a blood line integrally connected thereto for transporting whole blood from a donor to the separator, a plasma output port integrally connected to a plasma collection container by a plasma line, and a concentrated cell outlet port integrally connected to a reservoir for receipt of concentrated cells prior to reinfusion to the donor; ii) a donor line terminating in a venipuncture needle for transporting whole blood from a donor to the blood line, iii) an anticoagulant line integrally connected to the blood line and configured to be connected to a source of anticoagulant for transporting anticoagulant to the donor line, and iv) a reinfusion line for transporting concentrated cells from the reservoir to the donor line.

The reusable hardware component further comprises: i) a first peristaltic pump for delivering anticoagulant at a controlled rate into the blood line during a collection phase, ii) a second pump for delivering anticoagulated whole blood to the separator during the collection phase and for returning concentrated cellular components during a reinfusion phase, iii) a third pump for delivering concentrated cellular components from the separator to the reservoir during the collection phase, iv) a clamp associated with each of the blood line, plasma line, and reinfusion line, v) a weigh scale for weighing each of the plasma collection container, the reservoir and the source of anticoagulant, and vi) a programmable controller comprising a touch screen for receiving input from an operator, the programmable controller configured to receive a signal from each of the weigh scales and to automatically operate the first, second and third pumps and the clamps to separate whole blood into a plasma fraction and a concentrated cell fraction during the collection phase and to return concentrated cells to the donor during the reinfusion stage. The programmable controller is further configured to determine a target amount for the plasma product to be collected in the plasma collection container in accordance with any of the methods described herein, and to terminate the collection phase upon receiving a signal that the amount of plasma product in the plasma collection container equal to the target amount of the plasma product determined by the controller. In determining the target amount for the plasma product to be collected, the controller may be configured to calculate the hematocrit of the donor prior to the collection phase of each cycle. Alternatively, or additionally, the controller may receive a signal from a sensor or the like that is indicative of the donor's hematocrit. Further, the amount of plasma product in the plasma collection container may be determined by, e.g., the weigh scale associated with the plasma collection container or an optical sensor that directly measures the volume.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system is provided for performing a medical procedure with respect to a subject. The system includes a database, a user interface, a treatment device, and a controller. The database is pre-programmed with one or more subject data entries, each subject data entry having subject-specific information associated with it. The user interface is adapted to receive an identity input from a subject. The controller is associated or in communication with the database, the user interface, and the treatment device, and is configured to compare the identity input to the subject-specific information of the subject data entries. If the identity input corresponds to the subject-specific information of a subject data entry, the controller commands the treatment device to perform a medical procedure with respect to the subject. If the identity input does not correspond to the subject-specific information of any of the subject data entries, the controller generates an error signal that prevents the performance of the medical procedure with respect to the subject.

In another aspect, a method is provided for performing a medical procedure with respect to a subject. One or more subject data entries are stored, with each having subject-specific information associated with it. An identity input is received from the subject. The identity input is compared to the subject-specific information of the subject data entries. If the identity input corresponds to the subject-specific information of a subject data entry, a medical procedure is performed with respect to the subject. If the identity input does not correspond to the subject-specific information of any of the subject data entries, an error signal is generated to prevent the performance of the medical procedure with respect to the subject.

BRIEF DESCRIPTION OF THE DRAWINGS

FIG. 1 is a table showing the simplified nomogram presented in the FDA Memo: "Volume Limits-Automated Collection of Source Plasma (11/4/92)".

FIG. 7 is a table that shows the volume of raw plasma, based on donor hematocrit, that is contained within a plasma product volume limit set by the FDA nomogram using a 1:16 ratio of anticoagulant to whole blood.

FIG. 8 is a table that shows the volume of "unclaimed" raw plasma in the plasma product based the difference between the values set forth in FIG. 7 and the maximum volume of raw plasma that may be collected based on the FDA nomogram.

FIG. 9 is a table that shows the volume of plasma product that may be collected from a donor, based on the donor's weight and hematocrit, that results in the maximum permissible volume of raw plasma permitted by the FDA nomogram.

FIG. 10 is a table showing the inputs to a programmable controller for performing a hypothetical plasmapheresis procedure in accordance with the method of the present application.

FIGS. 11a, 11b comprise a table, broken into two parts illustrating how the donor's hematocrit increases over the course of a hypothetical plasmapheresis procedure based on the inputs from the table of FIG. 10, and resulting in an increase in the total collection volume of plasma product necessary to collect the target volume of raw plasma.

FIG. 16 is s schematic view of a further medical device according to an aspect of the present disclosure.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting and should be understood to encompass variations or embodiments that would occur to persons of ordinary skill.

In the context of the present application, plasmapheresis is performed on an automated system comprising a hardware component (or plasma collection device), generally designated 10, and a disposable set, generally designated 12, to collect plasma to be processed as source plasma. With reference to FIGS. 2-6, and as described in greater detail below, the disposable set 12 consists of an integrally connected separator, containers, and tubing to transport blood and solutions within a sterile fluid pathway.

Figure 2:
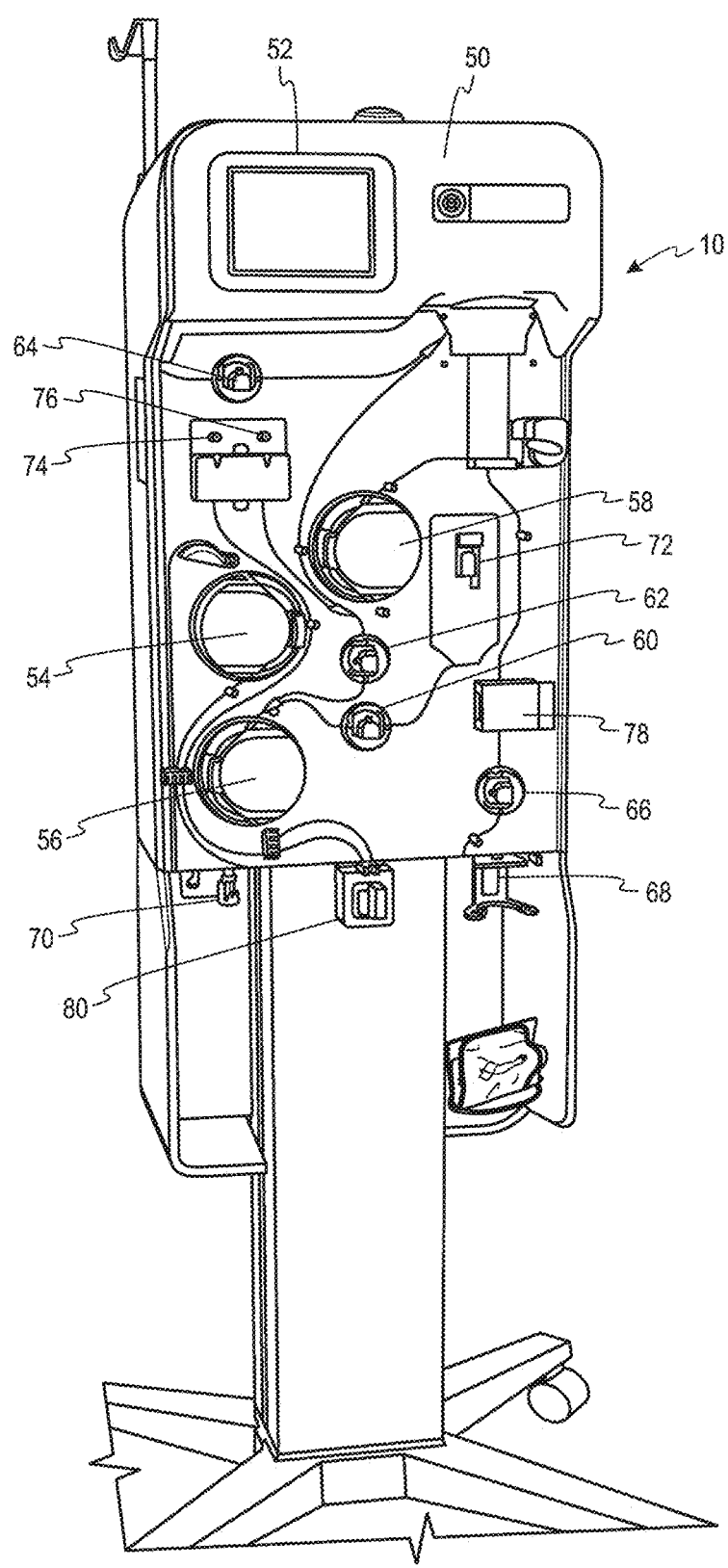
FIG. 2 is a perspective view of an exemplary plasmapheresis instrument suitable for use in the system and method of the present application.
Figure 3:
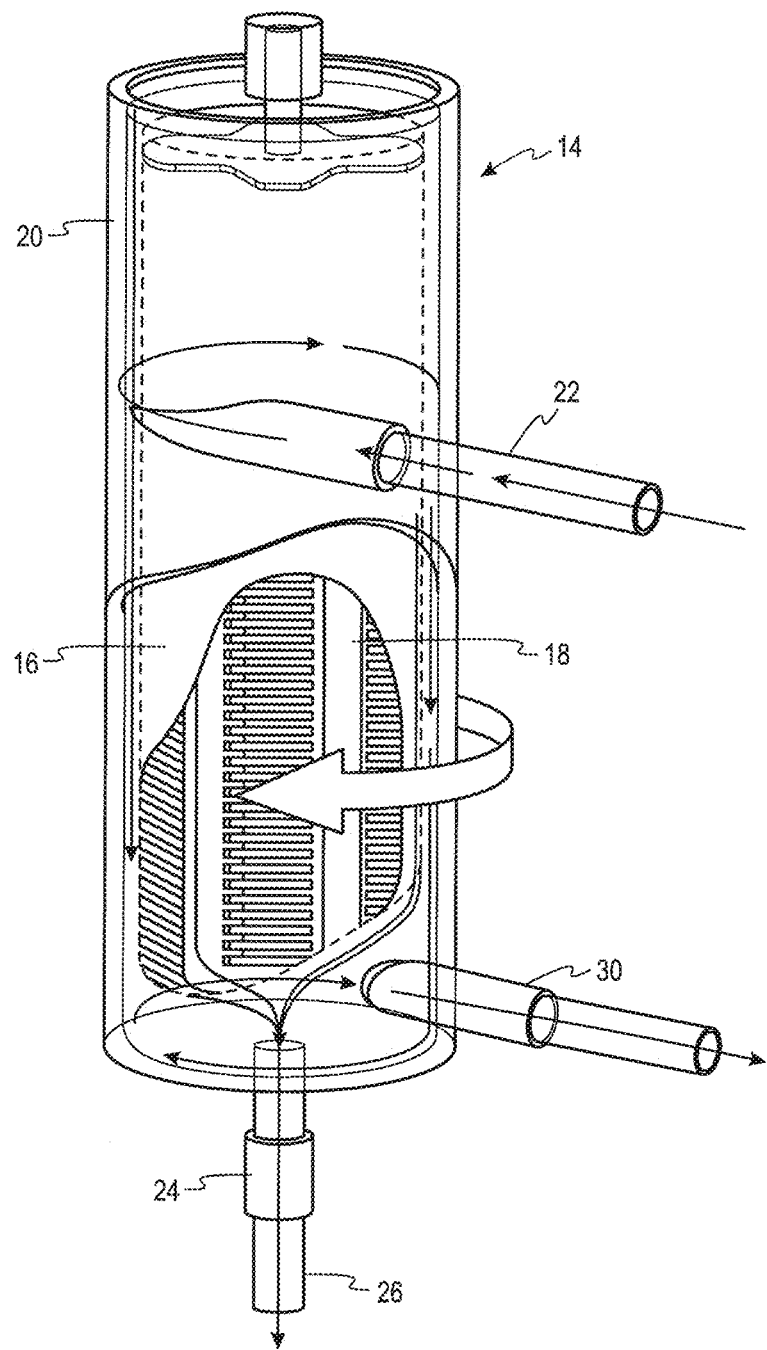
FIG. 3 is a perspective view of a spinning membrane separator of the type incorporated in a disposable set, with portions broken away to show detail, usable with the plasmapheresis system of FIG. 2.
Figure 4:
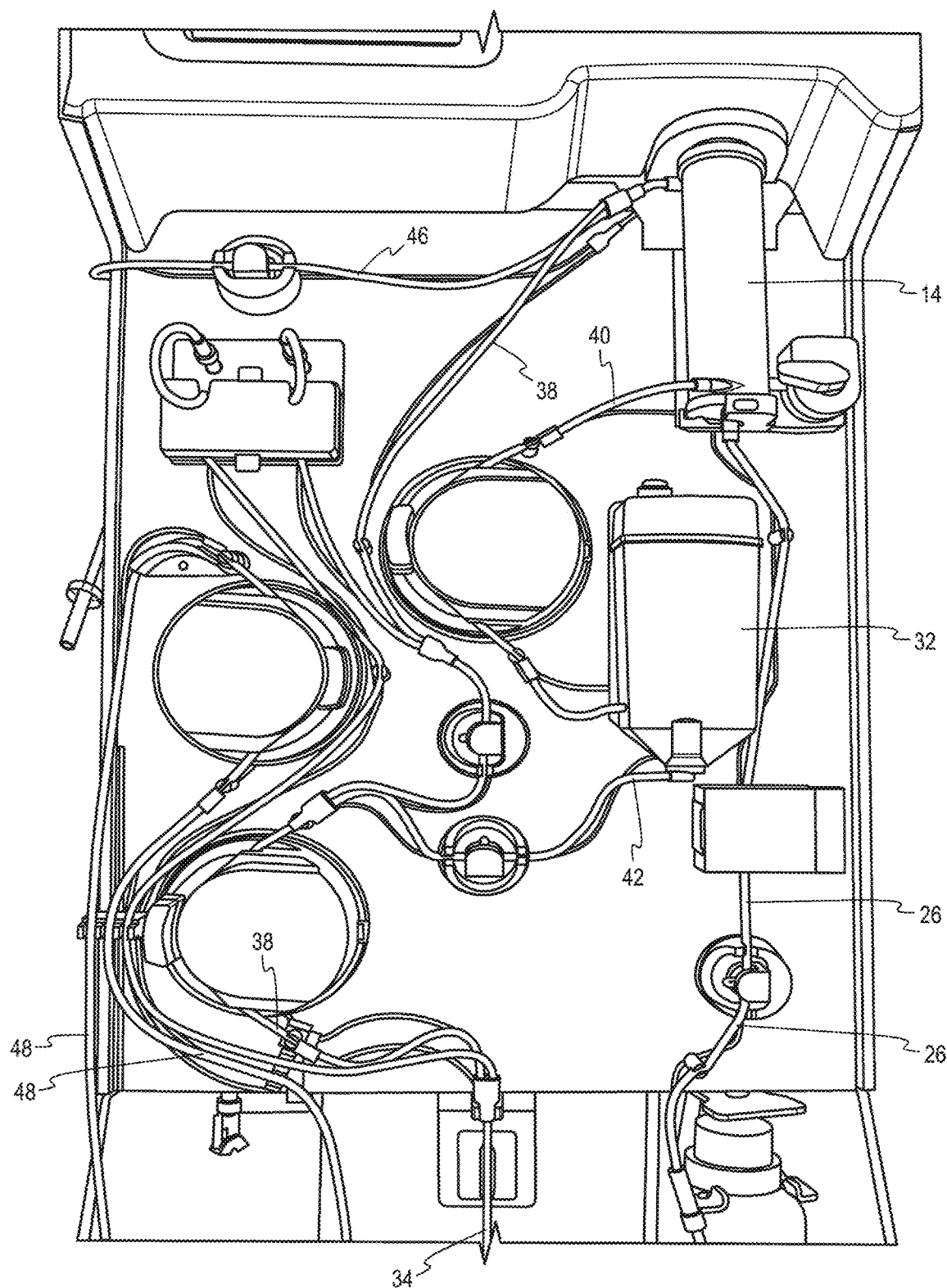
FIG. 4 is a perspective view of the front panel of the plasmapheresis system of FIG. 2 showing the components of the disposable set that are mounted thereto.
Figure 5:
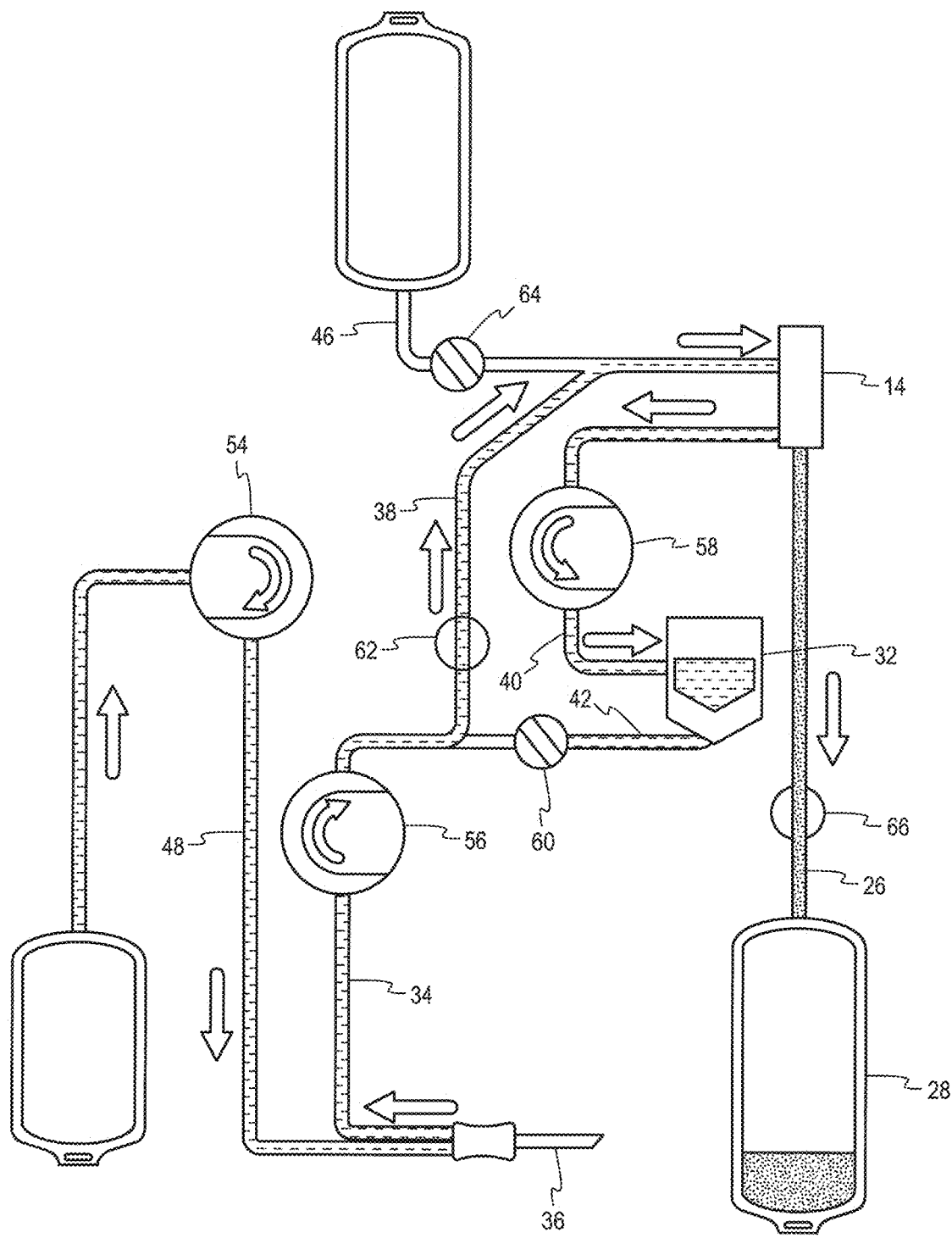
FIG. 5 is a schematic view showing operation of the plasmapheresis system in the collection phase.

The separator 14, best seen in FIG. 3, has a spinning membrane filter 16 mounted to a rotor 18 for rotation within a case 20 to separate blood into components. A detailed description of a spinning membrane separator may be found in U.S. Pat. No. 194,145 to Schoendorfer, which is incorporated herein by reference. As can be appreciated, in a different system, separation of the whole blood may be accomplished by centrifugation. See, e.g. U.S. Pat. No. 5,360,542 to Williamson et al.

During plasmapheresis, anticoagulated whole blood enters the separator 14 through a whole blood input port 22. The plasma is separated by the spinning membrane filter and then passes out of a plasma output port 24, through a plasma line 26, and into a plasma collection container 28. Concentrated cells are pumped out of a concentrated cell output port 30 into a reservoir 32, where the cells remain until reinfusion to the donor.

The disposable set 12 also includes tubing lines for introducing whole blood from the donor into the system during collection and returning concentrated cells to the donor during reinfusion (donor line 34, which terminates in the venipuncture needle 36), and for transporting anticoagulated whole blood to the separator (blood line 38), concentrated cells into the reservoir (cell line 40), concentrated cells from the reservoir to the donor line (reinfusion line 42), plasma into the plasma collection container (plasma line 44), saline (saline line 46), and anticoagulant (AC line 48).

The hardware component 10 includes a programmable controller 50 and touch screen 52 with a graphical user interface ("GUI") through which the operator controls the procedure. For example, the GUI permits entry of any of a donor ID, donor sex, donor height, donor weight, donor age, donor hematocrit/hemoglobin; a target saline infusion volume (if a saline protocol is selected), and a target plasma volume. The touch screen 52 also enables the operator to gather status information and handle error conditions. Controller 50 may comprise digital and/or analog circuit components (e.g., microprocessors, microcontrollers, application-specific integrated circuits, discrete components, surface-mount components, printed circuit boards and/or other circuits) configured (e.g., by being programmed) to perform functions described herein.

Three peristaltic pumps are located on the front panel of the hardware component 10, including an AC pump 54, a blood pump 56, and a cell pump 58. The AC pump 54 delivers anticoagulant solution (AC) at a controlled rate into the blood line 38 as whole blood enters the set from the donor. The blood pump 56 delivers anticoagulated whole blood to the separator during the collection phase of the procedure and returns concentrated cellular components and, if desired, replacement fluid to the donor during the reinfusion phase of the procedure. The cell pump 58 delivers concentrated cellular components from the separator 14 to a reservoir during the collection phase.

In one embodiment, the hardware component 10 is a blood processing device configured to separate plasma and formed elements from whole blood, where the whole blood line has a pump 56 to control the inlet flow and where there is an AC pump connected 54 to an AC line and where the plasma line is pump-free and the plasma is only being pushed to the plasma container.

The front panel also includes four clamps into which the disposable set 12 is installed, including a reinfusion clamp 60, a blood clamp 62, a saline clamp 64, and a plasma clamp 66. The reinfusion clamp 60 closes to block the reinfusion line (42) during the collection phase (FIG. 5) and is open during the reinfusion phase (FIG. 6) to allow the blood pump to reinfuse the concentrated cellular components from the reservoir 32 to the donor. The blood clamp 62 opens during the collection phase to allow anticoagulated whole blood to be pumped to the separator 14 and closes during the reinfusion phase to block the blood line 38. The saline clamp 64 closes to block the saline line 46 during the collection phase and during reinfusion of the separated cellular components. If saline is to be used as a replacement fluid, the saline clamp 64 opens during the reinfusion phase. The plasma clamp 66 opens during the collection phase to allow plasma to flow into the plasma collection container 28 and closes during the reinfusion phase.

The hardware component 10 includes three weigh scales to monitor the current plasma collection volume (scale 68), the AC solution volume (scale 70), and the concentrated cellular content volume (scale 72). The system also includes various sensors and detectors, including a venous pressure sensor 74, a separator pressure sensor 76, optical blood detectors 78, and an air detector 80.

Figure 6:
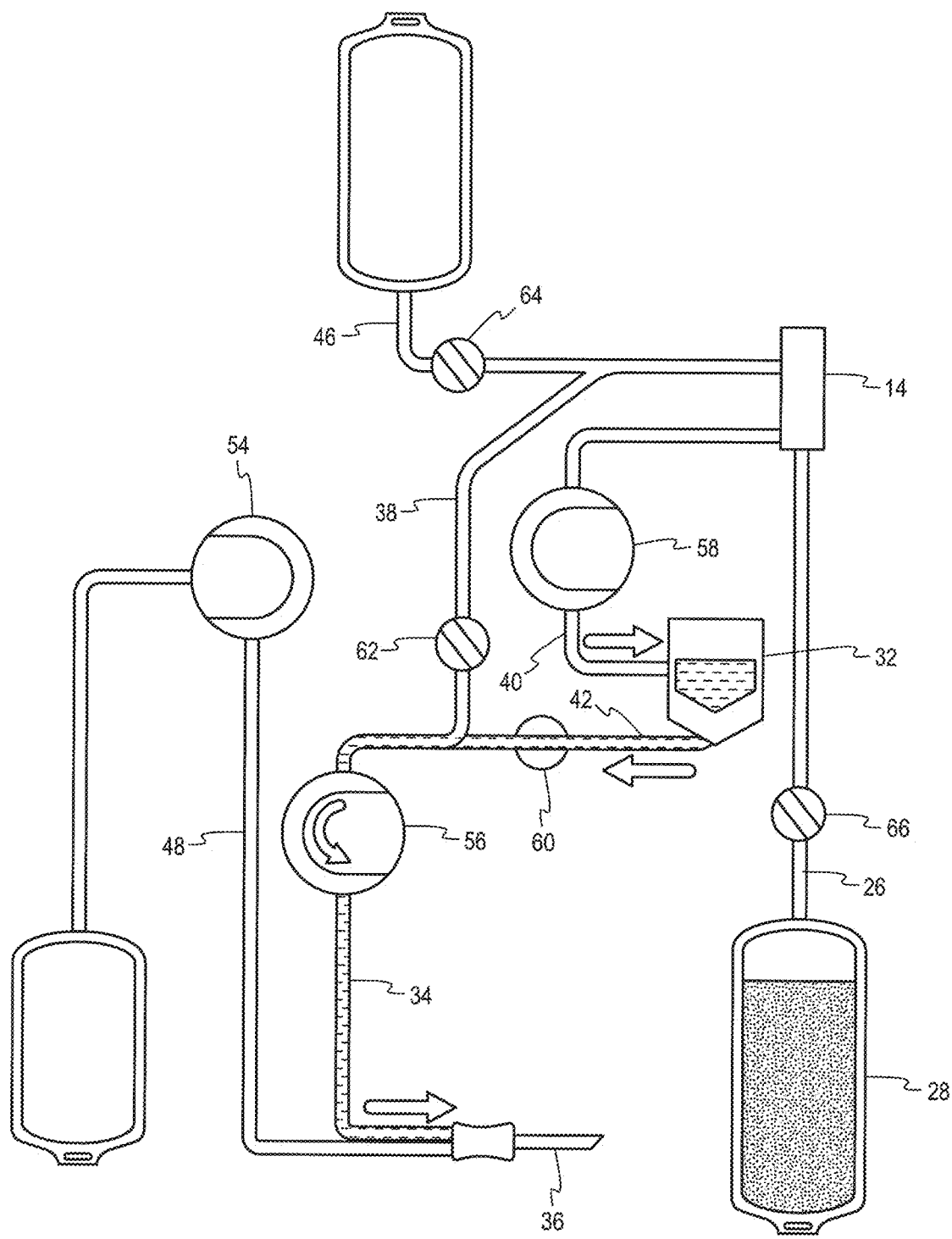
FIG. 6 is a schematic view showing operation of the plasmapheresis system in the reinfusion phase.

The donor is connected to the system throughout the procedure. As illustrated, the disposable set 12 includes a single venipuncture needle 36, through which whole blood is drawn from the donor in a collection phase (FIG. 5) and concentrated cells are returned to the donor in a reinfusion stage (FIG. 6). As noted above, the plasmapheresis procedure may comprise a plurality of cycles each having a collection/separation phase followed by a return or reinfusion phase. During the collection phase, the whole blood is separated into plasma and concentrated cells. The disposable set includes a plasma collection container 28 for receipt of the separated plasma and a reservoir 32 for receipt of the concentrated cells. During the reinfusion phase, the concentrated cells from the reservoir 32 are reinfused to the donor through the venipuncture needle 36. Typically, plasmapheresis performed with a single venipuncture needle 36 involves multiple cycles of collection and reinfusion.

Returning to FIG. 5, during the collection phase, anticoagulant solution (AC) is pumped at a controlled rate and mixed with whole blood as it enters the disposable set 12. The anticoagulated blood is pumped to the separator 14, where plasma is separated from the cellular components and directed to the plasma collection container 28.

The cellular components are pumped from the separator 14 to the reservoir 32. The collection phase stops when the reservoir 32 reaches an expected volume of concentrated cells or if the target plasma collection volume has been achieved.

Then, the reinfusion phase begins. With reference to FIG. 6, during the reinfusion phase, the blood pump 56 reverses direction and pumps the concentrated cells from the reservoir 32 back to the donor through the apheresis needle 36. If a saline protocol was selected, by which saline is returned to the donor as a replacement fluid for the collected plasma, the final reinfusion phase is followed by saline infusion.

In keeping with one aspect of the disclosure, the automated plasma collection device is configured to collect a volume/weight of anticoagulated plasma (i.e., the plasma product) having the maximum volume/weight of raw plasma permitted for the donor under the limits set forth in the FDA nomogram. In order to maximize the volume of raw plasma composing the plasma product, the device is programmed with a nomogram that accounts for the donor's hematocrit. With the knowledge of the donor's hematocrit and the instrument's AC ratio, the total volume/weight of plasma product to be collected can be determined such that the plasma product includes the maximum volume/weight of raw plasma fraction that may be collected from a donor, consistent with the limits for total volume/weight of raw plasma set forth in the FDA nomogram. By having the computations programmed into the controller, the likelihood of operator error is diminished in comparison to the off-line calculation of the collection volume that is then entered into the instrument.

During plasmapheresis, when anticoagulant is mixed with whole blood as it is drawn from the donor, the anticoagulant is evenly distributed within the raw plasma in the blood. However, the amount of raw plasma in the whole blood is dependent on the hematocrit (Hct) of the whole blood. The following relationships are established:

Volume of RBC=Volume of Whole Blood*Hct/100. [1]

Volume of Raw Plasma=Volume of Whole Blood*(1−Hct/100). [2]

When anticoagulant is mixed with the whole blood, it is typically metered at an AC Ratio (ACR) of 16 parts of whole blood to 1 part of AC, or at 1 part of whole blood to 0.06 parts of AC.

ACR=Volume of Whole Blood/Volume of Anticoagulant (the donor blood having no anticoagulant). [3]

(This yields a slightly different result from the FDA nomogram, which, as noted above, standardizes the volume of anticoagulant that may be added to a 1:16 ratio of anticoagulant to anticoagulated blood, or 0.06 parts anticoagulant to 1 part anticoagulated blood.)

Volume of Anticoagulated Blood=Volume of Anticoagulant+Volume of Whole Blood. [4]

Combining equations gives:

Volume of Raw Plasma=ACR*Volume of Anticoagulant*(1−Hct/100). [5]

Since the red cells are given back to the donor:

Volume collected Plasma=Volume of Raw Plasma+Volume of Anticoagulant. [6]

Equations [5] and [6] can be combined to calculate the amount of anticoagulant in a given amount of collected plasma:

Volume of Anticoagulant=Volume of collected plasma/(1+ACR*(1−Hct/100)). [7]

Further:

Volume of collected Plasma=Volume of Raw Plasma*K, where K=(ACR*(1−Hct/100)+1)/(ACR*(1−Hct/100)). [8]

In view of the relationships expressed in the equations above, the volume of raw plasma contained within the volume of plasma product permitted under the FDA nomogram can be determined based upon the hematocrit of the donor. The results of such calculations are set forth in FIG. 7, which shows the volume of raw plasma based on donor hematocrit that is contained within a plasma product volume limit set by the FDA nomogram.

As can be appreciated with reference to FIG. 7, for donors weighing from 110 to 149 lbs. (for whom the maximum plasma product volume per the FDA nomogram is 690 mL), if the donor has a hematocrit of 42 or greater, the volume of raw plasma collected is less than the 625 mL permitted by the FDA nomogram. The situation is similar for donors having a weight of 150 to 174 lbs. (for whom the maximum plasma collection volume per the FDA nomogram is 825 mL) and for donors having a weight of 175 lbs. and up (for whom the maximum plasma collection volume per the FDA nomogram is 880 mL) when the donor's hematocrit is 40 or greater.

The table set forth in FIG. 8 presents the volume of "unclaimed" raw plasma in the plasma product based the difference between the values set forth in FIG. 7 and the maximum volume of raw plasma that may be collected based on the FDA nomogram. Thus, as shown in the table set forth in FIG. 9, the plasma product collected from any particular donor may be adjusted from that set forth in the FDA nomogram by an amount corresponding to the amount of "unclaimed" raw plasma set forth in FIG. 8 plus the amount of anticoagulant needed to process the additional volume.

Alternatively, the volume of plasma product to be collected may be calculated by first determining a weight and hematocrit (Hct) for the donor; determining the volume of raw plasma ($V_{RP}$) that may be collected based on the weight of the donor ($W_{kg}$); determining a ratio K between the $V_{PP}$ and the $V_{RP}$, such that K=$V_{PP}$/$V_{RP}$, based on an anticoagulant ratio (ACR; 1:16 or 0.06:1, per the FDA nomogram) and the Hct of the donor; and determining $V_{PP}$, such that $V_{PP}$=$V_{RP}$*K. Further, K=(ACR*(1−Hct/100)+1)/(ACR*(1−Hct/100)).

In a further alternative, the volume of plasma product that is to be collected ($V_{PP}$) may be calculated by first determining the weight ($W_{kg}$) and hematocrit (Hct) of the donor; determining the volume of raw plasma ($V_{RP}$) that may be collected based on the weight of the donor ($W_{kg}$); determining the volume of anticoagulant to be added ($V_{AC}$) based on the anticoagulant ratio (ACR; 1:16 or 0.06:1, per the FDA nomogram) and the hematocrit of the donor such that $V_{AC}$=$V_{RP}$*(ACR*(1−Hct/100)); and determining the collection volume such that $V_{PP}$=$V_{RP}$+$V_{AC}$.

Various methods may be used for determining the volume of raw plasma that may be collected based on the weight of the donor. For example, the weight of the donor may be multiplied by an established constant "$K_1$" (such as 10 mL/kg). Alternatively, the weight of the donor may be segregated into weight categories, with a fixed volume established for each category (as in the FDA nomogram discussed above, in which the ranges of donor weight are divided into three categories).

Alternatively, a donor's plasma volume may be estimated based on the donor's total blood volume, and a volume of plasma that may be harvested consistent with donor safety and comfort may be based on this estimation. Methods utilizing donor parameters may be used to estimate a donor's total blood volume. Examples of such methods include Nadler's equations (that take into account the height, sex and weight of the donor), Gilcher's Rule of Five (that takes into account sex, weight and morphology (obese, thin, normal or muscular), or the standards of the International Counsel for Standardization in Haematology ("ICSH") as set forth in Br. J. Haem. 1995, 89:748-56) (that take into account the height, weight, age and sex of the donor). Any other generally accepted methodology for determining donor's total blood volume may also be used, such as that disclosed in Lemmens et al, "Estimating Blood Volume in Obese and Morbidly Obese Patients," Obesity Surgery, 16, 773-776, 2006:

$$InBv = \frac{70}{\sqrt{BMIp/22}}$$

In which $_{In}Bv$ is indexed blood volume and $BMI_p$ is the body mass index of the patient, based on patient weight and height. An age-dependent regression equation may also be used for indexed blood volume $_{In}BV$ at IBW (ideal body weight), as shown below:

$_{In}BV$=90−0.4×age (males); $_{In}BV$=85−0.4×age (females). Thus, the indexed blood volume may be calculated based on sex of the donor.

Once the donor's total blood volume is determined, the donor's plasma volume may be estimated by multiplying the total blood volume by a constant "$K_2$", where or $K_2$ equals (1−Hct of the donor).

From an analysis of demographic, examination, and laboratory data from the 2015-2016 National Health and Nutrition Examination Survey, in which sex, age, height, weight, pregnancy data and hematocrit were extracted, presented in Pearson et al., Interpretation of measured red cell mass and plasma volume in adults: Expert Panel on Radionuclides of the International Council for Standardization in Haematology, British J. Haematology, 89: 748-756 (1995), (upon which the ICSH recommended formulae were derived), it has been determined that for donors having certain characteristics (namely low weight females with high hematocrits), up to 36% of the available plasma may be collected while staying within current regulations. Plasmapheresis procedures with such donors have been carried out routinely without adverse reactions, and thus are considered safe. This suggests that up to 36% of a donor's available plasma can be safely collected in a plasmapheresis procedure.

Given that only negative deviations of a donor's true blood volume from a predicted/calculated total blood volume present a potential risk, a further adjustment downward of the harvestable volume of plasma may be appropriate. Based on a consideration of the deviation between the calculated blood volume as determined in Pearson et al., cited above, and the experimental blood volume data presented in Retzlaff et al., Erythrocyte Volume, Plasma Volume, and Lean Body Mass in Adult Men and Women, J. Haematology, 33, 5:649-667 (1969), there is a 95% confidence that an individual's predicted blood volume will differ not more that 20.5%. Thus, a scaling factor of 0.795 may be applied to determination of harvestable raw plasma being 36% of the donor's total plasma volume described above, so that 28.6% of a donor's calculated volume of raw plasma may be harvested, consistent with donor safety and comfort.

Alternatively, an adjustment $V_C$ may be made to the calculated volume of whole blood $V_{WB}$ before calculating the volume of harvestable plasma $V_{RP}$, such the $V_{RP}$=0.36 (1−Hct)($V_{WB}$−$V_C$). A regression analysis of the data presented by Retzlaff resulted in a determination of $V_C$=523 mL.

Thus, the collection volume (the volume of plasma product) is determined based on the volume of raw plasma volume that may be collected from a particular donor, the donor's hematocrit, and the fixed anticoagulant ratio (ACR). Consequently, this methodology allows for more consistent control for the raw plasma volume of the donor, which is the variable most related to donor safety.

In practice, the operator enters into the system controller the collection volume for the plasma product for the particular donor, based on the target volume of raw plasma that may be harvested. The target plasma collection volume may be as set forth in FIG. 9, based on the donor's weight and hematocrit for the initial collection phase, or by any of the other methods as set forth above. Alternatively, the controller is configured to calculate the target plasma product collection volume for the initial collection phase in accordance with a methodology such as those described above upon the operator entering, e.g., the donor's weight and hematocrit, and/or any of the additional donor-specific information (such as the donor's sex, height and age) required by the methodologies used for determining a donor's total blood volume, total plasma volume, and the target volume of harvestable plasma that may be collected. In a further alternative, the plasma collection device may be integrated with a donor management system, by which donor parameters used for qualification screening (such as weight, hematocrit, etc.) can be electronically sent to the instrument, eliminating the opportunity for operator error in entering the donor parameters. The donor management system could also utilize the donor screening measurements, along with the relationship between raw plasma volume and collection volume, to automatically calculate a plasma collection volume that it would transmit to the controller of the plasmapheresis device. Parameters of all types (e.g., weight, height, sex, hematocrit, name, birthdate, target volume for plasma product, target volume for raw plasma, anticoagulant ratio, collection type, blood component to be collected, etc.) may be retrieved by controller 50 of hardware 10 from another database (e.g., a central or remote database) which may be remote from hardware component 10, for example using the embodiments described herein with reference to FIGS. 13 and 14. A remote database may be a donor management system, such as one used for donor screening prior to a donation, donor recruitment, and/or donor record management. Controller 50 may be configured to retrieve or download parameters from the remote database over one or more wired and/or wireless networks, such as a local area network, a wide area network, an Ethernet, a Wi-Fi network using an IEEE 802.11x standard, or other networks.

As noted above, plasmapheresis procedures are performed with multiple cycles of collection/draw phases and return/reinfusion phases. If the return/reinfusion phase does not include reinfusion of a replacement fluid, the donor's hematocrit will increase from one cycle to the next. Consequently, if the target volume for plasma product is determined based only on the donor's initial hematocrit, and does not take into account the donor's increasing hematocrit, the volume of anticoagulant in the plasma product will be greater (and the volume of raw plasma less) than what was predicted by the initial calculation for determining the target volume of plasma product. Thus, in order to ensure that the volume of plasma product that is collected contains the maximum volume of raw plasma that was determined to be harvested from a particular donor, the target volume for plasma product is recalculated periodically throughout the plasmapheresis procedure, such as before the start of the collection phase of each cycle, to take into account the change in the donor's hematocrit.

Accordingly, a determination of the target volume for plasma product based on the donor's starting hematocrit is made. The plasmapheresis procedure commences with a first draw phase until a specified volume of whole blood (typically approximately 500 mL) has been withdrawn from the donor. Anticoagulant is added to the whole blood and the anticoagulated whole blood is separated into a plasma product, red blood cells, and other non-RBC blood components. At the conclusion of the first draw phase, the red blood cells and non-RBC blood components are returned to the donor. The current volume of plasma product collected after the first draw phase is determined by, e.g., the weigh scale. Then a current value for the hematocrit of the donor is established and a new target volume of plasma product to be collected is determined, and the second cycle of draw and return phases is performed. The cycle of draw and return phases is repeated until the target volume of plasma product for the plasmapheresis procedure is collected, as recalculated prior to the start of each draw phase. After the final collection phase, the controller initiates the final red blood cell reinfusion stage, after which the donor is disconnected.

The benefits of performing a plasmapheresis procedure having multiple collection/reinfusion cycles in accordance with the methodology set forth above may be seen by reference to the tables of FIGS. 10 and 11a, 11b. FIG. 10 displays the input data for a hypothetical plasmapheresis procedure for a donor weighing 190 lbs. (86.4 kg) and having an initial hematocrit of 44. With reference to the table of FIG. 1, the simplified FDA nomogram would limit the volume of plasma to be collected from such a donor to 800 mL, and the total collection volume for the plasma product to 880 mL. In the present example, the FDA nomogram limit on the volume of raw plasma that may be collected is for illustrative purposes only. As set forth above, other methodologies may be used to determine the amount of raw plasma that may be safely extracted from a donor that would differ from that indicated by the FDA nomogram.

The number of collection and reinfusion cycles in a plasmapheresis procedure may vary from three to twelve. In the hypothetical plasmapheresis procedure, there are five collection and reinfusion cycles, which are chosen for illustrative purposes.

Before the commencement of the first collection cycle, the volume of raw plasma to be collected and the total target volume of plasma product to be collected are determined in accordance with the methodologies described above, based on the donor's initial hematocrit. As set forth in the first row of the table (Cycle 1 start), the initial target volume for the plasma product to be collected is 889 mL, which is the same as indicated by the table of FIG. 9 for a donor having a weight of 175 lbs. and up and a hematocrit of 44 in order to harvest the FDA limit of 800 mL of raw plasma from the donor.

During each collection phase, 500 mL of whole blood is drawn from the donor, to which anticoagulant is added at a predetermined ratio (i.e., 1:16), such that 31 mL is added for each collection cycle of 500 mL. The whole blood plus anticoagulant is separated into a plasma fraction and a red blood cell fraction.

During the first return phase (Cycle 1 return end), the red blood cells and "non-RBC" blood components are returned to the donor, so that at the end of the first return cycle the donor's hematocrit has increased to 45.6%, as calculated by the controller based on a blood volume being decreased by the amount of raw plasma collected, while the quantity of red blood cells in the total blood volume remains the same as at the start of the procedure. The controller can also account for the volume of anticoagulant that is reinfused in each return phase along with the red blood cells, as well as the residual anticoagulant in the donor's whole blood being drawn in cycles 2 and following, when determining the new hematocrit value for the next cycle. The volume of raw plasma and the total target volume of plasma product to be collected for the procedure are then recalculated based on the donor's new, increased hematocrit and raw plasma volume. This provides for a new total target collection volume of 891 mL.

The second collection phase is then performed, resulting in a total of 430 mL of plasma product comprising 386 mL of raw plasma being collected over the first two collection phases (Cycle 2 draw end). The red blood cells and "non-RBC" blood components are again returned to the donor, after which the donor's hematocrit is calculated to be 47.2%.

Two more collection phases of 500 mL are performed, each followed by a return phase, in which new values for the volume of raw plasma and total volume of plasma product to be collected are determined before the start of each collection phase. With the increasing hematocrit of the donor, the recalculated target collection volume for procedure increases to 893 mL (for the third collection phase) and then to 894 mL (for the fourth collection phase). A fifth "mini" collection cycle is performed to bring the volume of raw plasma collected up to the 800 mL permitted by the FDA nomogram for the hypothetical donor. The recalculated target collection volume of plasma product for the fifth collection phase remains at 894 mL.

Thus, as illustrated in the example above, when the target collection volume for the plasma product is recalculated for each collection phase, a target collection volume for the plasma product of 894 mL is obtained, which is required in order to collect the target volume of raw plasma of 800 mL. In contrast, 889 mL of plasma product would have been collected if the target collection volume is determined based only on the donor's initial hematocrit, or 880 mL if the target collection volume is based on the simplified FDA nomogram. In both cases, less than the target volume of 800 mL would have been collected.

As can be appreciated, the greater the accuracy with which the hematocrit of the donor can be determined, both before and during the procedure, the more likely the target volume of plasma product collected will include the maximum volume of raw plasma that can be collected for a particular donor. As described above, the hematocrit of the donor during the procedure is based on the assumptions that 100% of the red blood cells that are withdrawn in each draw cycle are reinfused in each return cycle, along with 100% of the non-RBC cellular products and a volume of anticoagulant. However, it has been determined that during the course of a blood separation procedure, interstitial fluid can shift to the intravascular space, resulting in restoring half of the withdrawn volume. See, Saito et al., Interstitial fluid shifts to plasma compartment during blood donation. Transfusion 2013; 53(11):2744-50. The shifted interstitial fluid is in addition to the red blood cells, non-RBC cellular products, and anticoagulant that are reinfused in each return phase. Thus, accounting for the shift of interstitial fluid would result in a more accurate hematocrit determination, and thus a more accurate determination of the target volume for plasma product that will result in the maximum amount of raw plasma.

The shift of interstitial fluid during plasmapheresis has been substantiated by tracking the level of Immunoglobulin G (IgG) of a donor over the course of a plasmapheresis procedure. See, e.g., Burkhardt et al., Immunoglobulin G levels during collection of large volume plasma for fractionation; Transfusion 2017; 56:417-420. If no interstitial fluid was being shifted, the IgG level of the donor would be stable over the course of the plasmapheresis procedure. However, the IgG level has been shown to drop, and the amount that the IgG level drops is a function of the volume of interstitial fluid that has shifted to the blood system.

Figure 12:
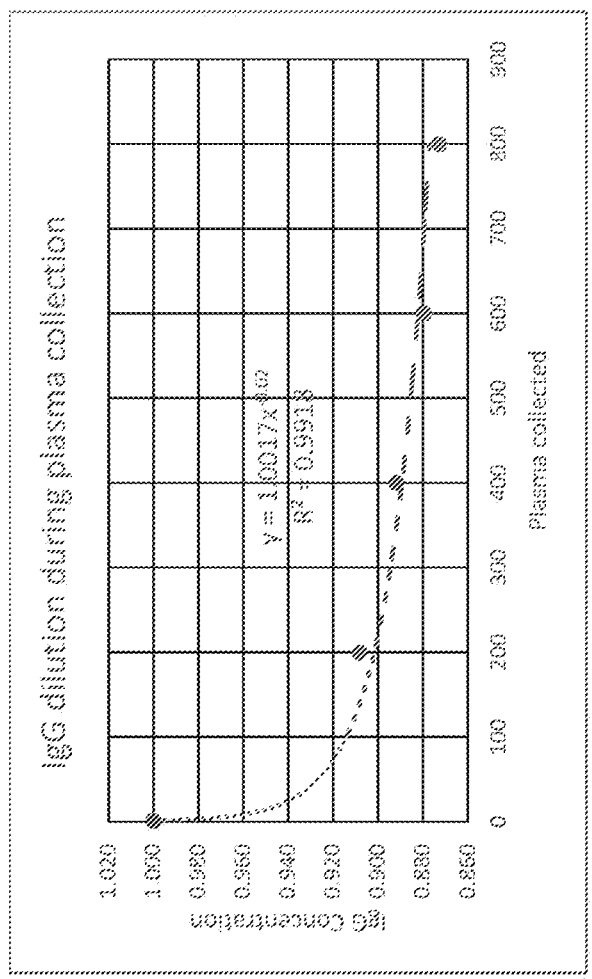
FIG. 12 is a graph illustrating IgG dilution during plasmapheresis.

With reference to FIG. 12, a plot of volume of plasma collected (along the X-axis versus IgG concentration (along the Y-axis) that was developed empirically is shown. A 9% drop of the donor's IgG is seen from the baseline of zero plasma collected (at the start of the procedure) to 200 mL of plasma collected, and a drop of an additional 4% from 200 mL to 800 mL collected. This was attributable to a shift of interstitial fluid equal to approximately 9% of the donor's initial total blood volume (after 200 mL of plasma being collected) to approximately 13% of the donor's initial total blood volume (after 800 mL of plasma being collected).

Based on the plot of FIG. 12, the following relationship between the amount that the donor's IgG concentration and the volume of plasma collected has been established: $y=1.0017x^{-0.02}$, where y=IgG concentration and x=plasma volume collected. Thus, the percentage of the donor's blood volume that is replaced by the shift of interstitial fluid is equal to $V_b(1-y)$, where $V_b$ is the donor's initial volume of whole blood. Thus, the shifted volume of interstitial fluid can be calculated based on the volume of plasma collected, and this amount can be added to the volume of red blood cells, non-RBC cellular products and anticoagulant reinfused in each return phase to determine the current total blood volume, and thus hematocrit, of the donor. As can be appreciated, the controller can be configured to automatically determine the volume of interstitial fluid that has shifted based on the volume of plasma collected, and to include the shifted volume when determining the donor's hematocrit prior to each draw phase.

Alternatively, other methods that directly measure the donor's hematocrit may be employed, such as an optical sensor or, if a centrifugal separator is being used, measuring the volume of red blood cells in the centrifuge.

In addition, anticoagulant is commonly introduced into the disposable kit prior to the commencement of the plasmapheresis procedure in pre-processing steps, such as for priming the disposable kit, performing one or more pre-cycles, or for performing other pre-procedure steps. To the extent that anticoagulant used for these purposes is ultimately directed to the plasma product collection container, it should be accounted for in determining the volume contained in the plasma collection container that results in the target volume of raw plasma being collected. This may be done, for example, by measuring the weight of the "full" container of anticoagulant and the weight of the container of anticoagulant prior to the commencement of the first draw cycle and adding that volume of anticoagulant to the target volume of plasma product. The controller can be configured to automatically perform the steps necessary to account for the anticoagulant introduced into the plasma collection container separately from the anticoagulated plasma.

The methods and system set forth above have several aspects. In a first aspect, a method for collecting plasma in which plasma product is collected in multiple collection phases between which separated red blood cells are reinfused to the donor is provided. The method of this first aspect comprises a) determining a volume of whole blood ($V_b$) and hematocrit (Hct) for a donor; b) determining a volume of raw plasma ($V_{RP}$) that may be collected from the donor; c) determining a volume of plasma product ($V_{PP}$) that may be collected, wherein the plasma product comprises the raw plasma volume plus a volume of anticoagulant; d) withdrawing whole blood from the donor; e) introducing anticoagulant into the withdrawn whole blood at a specified ratio (ACR); f) separating the withdrawn whole blood into a plasma product and a second component comprising red blood cells; g) collecting the plasma product in a plasma collection container; h) after a desired amount of whole blood has been withdrawn from the donor, returning the red blood cells to the donor; and i) determining the Hct of the donor and $V_{PP}$ prior to each collection phase.

In a second aspect, steps d)-i) are continued until a measured volume of plasma product in the collection container equals $V_{PP}$.

In a third aspect, a method for collecting plasma in which plasma product is collected in multiple collection phases between which separated red blood cells are reinfused to the donor is provided. The method of this second aspect comprises: a) determining a volume of whole blood ($V_b$) and hematocrit (Hct) for a donor; b) determining a volume of raw plasma ($V_{RP}$) that may be collected from the donor based on $V_b$; c) determining a volume of anticoagulant $V_{AC}$ to be added to the $V_{RP}$ based on an anticoagulant ratio (ACR) and the Hct of the donor, such that $V_{AC}=V_{RP}*(ACR*(1-Hct))$; d) determining a volume of plasma product ($V_{PP}$) that may be collected, wherein the plasma product comprises the raw plasma volume ($V_{RP}$) plus the volume of anticoagulant ($V_{AC}$); e) withdrawing whole blood from the donor; f) introducing anticoagulant into the withdrawn whole blood at the specified ratio (ACR); g) separating the withdrawn whole blood into a plasma product and a second component comprising red blood cells; h) collecting the plasma product in a plasma collection container; i) after a desired amount of whole blood has been withdrawn from the donor, returning the red blood cells to the donor; and j) determining the Hct of the donor and $V_{PP}$ prior to each collection phase.

In a fourth aspect, steps d)-j) are continued until a measured volume of plasma product in the collection container equals $V_{PP}$.

In a fifth aspect, $V_b$ is determined based on one or more donor specific characteristics including a donor's weight, height, sex, age, and morphology.

In a sixth aspect, a method is provided for collecting a volume of plasma product ($V_{PP}$) in an apheresis procedure in which plasma product is collected in multiple collection phases between which separated red blood cells are reinfused to the donor. In the method of this fourth aspect, $V_{PP}$ is equal to a volume of raw plasma ($V_{RP}$) that may be collected from a donor plus a volume of anticoagulant ($V_{AC}$) that is added to the $V_{RP}$ during the apheresis procedure. The steps of the method comprise: a) determining a weight ($W_{kg}$) and sex (M or F) for the donor; b) determining a hematocrit (Hct) for the donor; c) determining the volume of raw plasma ($V_{RP}$) that may be collected based on the weight ($W_{kg}$) and sex (M or F) of the donor; d) determining a ratio K between the $V_{PP}$ and the $V_{RP}$, such that $K=V_{PP}/V_{RP}$, based on an anticoagulant ratio and the Hct of the donor; e) determining $V_{PP}$, such that $V_{PP}=V_{RP}*K$; f) withdrawing whole blood from the donor; g) introducing anticoagulant into the withdrawn whole blood at a specified ratio (ACR); h) separating the withdrawn whole blood into a plasma product and a second component comprising red blood cells; i) collecting the plasma product in a plasma collection container; j) after a desired amount of whole blood has been withdrawn from the donor, returning the red blood cells to the donor; and k) determining the Hct of the donor and the target $V_{pp}$ prior to each collection phase.

In a seventh aspect, steps c)-k) are repeated until a measured volume of plasma product in the collection container equals $V_{PP}$. Preferably, $K=V_{PP}/V_{RP}=(ACR*(1-Hct/100)+1)/(ACR*(1-HCT/100))$.

In an eighth aspect, a method is provided for collecting a volume of plasma product ($V_{PP}$) in an apheresis procedure in which plasma product is collected in multiple collection phases between which separated red blood cells are reinfused to the donor. In this fifth aspect $V_{PP}$ is equal to a volume of raw plasma ($V_{RP}$) that may be collected from a donor plus a volume of anticoagulant ($V_{AC}$) that is added to the $V_{RP}$ during the apheresis procedure. The steps of the method comprise: a) determining a weight ($W_{kg}$) and sex (M or F) for the donor; b) determining a hematocrit (Hct) for the donor; c) determining the volume of raw plasma ($V_{RP}$) that may be collected based on the weight of the donor ($W_{kg}$) and the sex (M or F) of the donor; d) determining the $V_{AC}$ to be added to the $V_{RP}$ based on an anticoagulant ratio (ACR) and the Hct of the donor, such that $V_{AC}=V_{RP}*(ACR*(1-Hct))$; e) determining $V_{PP}$, such that $V_{PP}=V_{RP}+V_{AC}$; f) withdrawing whole blood from the donor; g) introducing anticoagulant into the withdrawn whole blood at a specified ratio (ACR); h) separating the withdrawn whole blood into a plasma product and a second component comprising red blood cells; i) collecting the plasma product in a plasma collection container; j) after a desired amount of whole blood has been withdrawn from the donor, returning the red blood cells to the donor; and k) determining the Hct of the donor and $V_{PP}$ prior to each collection phase.

In a ninth aspect, steps d)-k) are continued until a measured volume of plasma product in the collection container equals $V_{PP}$.

In a tenth aspect, $V_{RP}$ is determined by establishing the $V_{RP}$ for each of a plurality of ranges of donor weight and selecting the $V_{RP}$ for the range of weight that is inclusive of the weight of the donor. The ranges of donor weight may be in three categories from 110 to 149 lbs., 150 to 174 lbs., and 175 lbs. and up.

In an eleventh aspect, $V_{RP}=K_1*W_{kg}$.

In a twelfth aspect, $V_{RP}$ is no greater than 28.6% of $(1-Hct)*(V_b)$.

In a thirteenth aspect, $V_b$ is determined using one of Nadler's equations, Gilcher's Rule of Five, the standards of the ICSH, and any other generally accepted methodology.

In a fourteenth aspect, $V_{RP}=W_{kg}*10$ mL/kg.

In a fifteenth aspect, when donor parameters are used to estimate a total blood volume ($V_b$) for the donor, $V_{RP}=K_2*V_b$.

In a sixteenth aspect, an automated system for separating plasma from whole blood is provided comprising a reusable hardware component and a disposable kit. The disposable kit further comprises i) a separator for separating whole blood into a plasma fraction and a concentrated cell fraction, the separator having an input having a blood line integrally connected thereto for transporting whole blood from a donor to the separator, a plasma output port integrally connected to a plasma collection container by a plasma line, and a concentrated cell outlet port integrally connected to a reservoir for receipt of concentrated cells prior to reinfusion to the donor; ii) a donor line terminating in a venipuncture needle for transporting whole blood from a donor to the blood line, iii) an anticoagulant line integrally connected to the blood line and configured to be connected to a source of anticoagulant for transporting anticoagulant to the donor line, iv) a saline line configured to be attached to a source of saline for transporting saline to the blood line, and v) a reinfusion line for transporting concentrated cells from the reservoir to the donor line. The reusable hardware component further comprises: i) a first peristaltic pump for delivering anticoagulant at a controlled rate into the blood line during a collection phase, ii) a second pump for delivering anticoagulated whole blood to the separator during the collection phase and for returning concentrated cellular components during a reinfusion phase, iii) a third pump for delivering concentrated cellular components from the separator to the reservoir during the collection phase, iv) a clamp associated with each of the blood line, plasma line, reinfusion line and saline line, v) a weigh scale for weighing each of the plasma collection container, the reservoir and the source of anticoagulant, and vi) a programmable controller comprising a touch screen for receiving input from an operator, the programmable controller configured to receive a signal from each of the weigh scales and to automatically operate the first, second and third pumps and the clamps to separate whole blood into a plasma fraction and a concentrated cell fraction during the collection phase and to return concentrated cells to the donor during the reinfusion stage. The programmable controller is further configured to determine the weight of the plasma fraction to be collected in the plasma collection container in accordance with any of the aspects described herein, and to terminate the collection phase upon receiving a signal from the weigh scale for the plasma collection container equal to the weight of the plasma fraction determined by the controller. In determining the target amount for the plasma product to be collected, the controller may be configured to calculate the hematocrit of the donor prior to the collection phase of each cycle. Alternatively, or additionally, the controller may receive a signal from a sensor or the like that is indicative of the donor's hematocrit. Further, the amount of plasma product in the plasma collection container may be determined by, e.g., the weigh scale associated with the plasma collection. In one embodiment, the separator comprises a spinning membrane separator.

Figure 13:
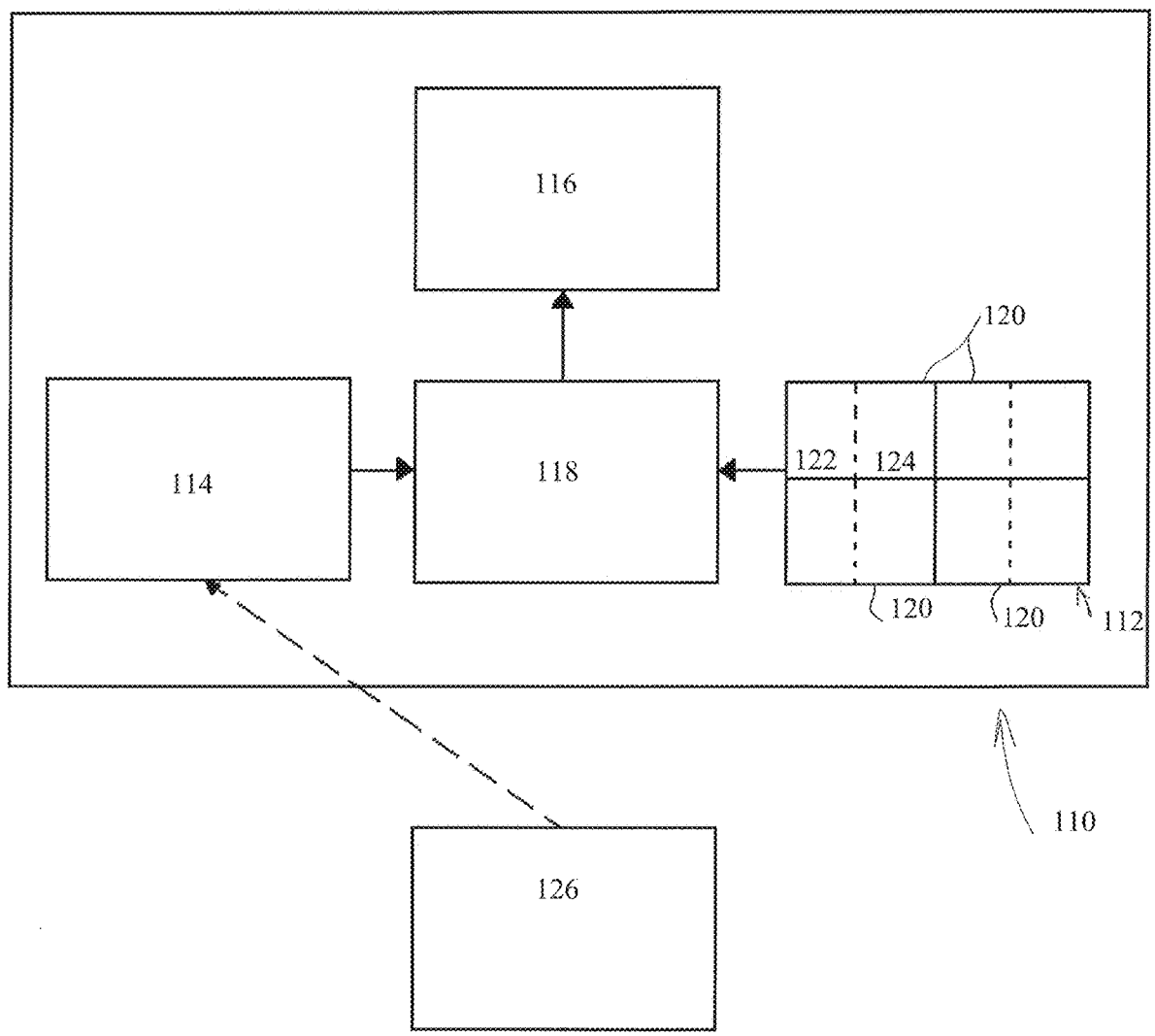
FIG. 13 is a schematic view of a medical device according to an aspect of the present disclosure.

FIG. 13 diagrammatically illustrates a system 110 for performing a medical procedure with respect to a subject. One or more features, functions or components of the embodiments of FIGS. 13 and 14 may be combined with one or more features, functions or components of the embodiments of FIGS. 1 through 12 to provide further embodiments. The system 110 of FIG. 13 includes a data storage location (such as a database 112), a user interface 114, a treatment device 116, and a controller 118. The system may be configured and used for carrying out any particular medical procedure. More particularly, the system may be configured for carrying out automated or semi-automated apheresis or blood collection procedures on a healthy donor or patient, such as a plasmapheresis procedure as described above.

The data storage location may be variously configured and positioned without departing from the scope of the present disclosure. For example, the data storage location may be integrated into the system 110 and associated with the controller 118, as is the case with the database 112 of FIG. 13. In other embodiments, the data storage location may be remote from the system 110, for example, being located at or in a central server or storage facility of the owner of the system 110. If the data storage location is remotely located, it may communicate with the system 110 by any of a number of known or novel remote access means such as, but not limited to, wireless Internet access. In another embodiment, the data storage location is a removable storage device, such as an encoded identification card, which may be brought into association with the system 110 by a subject or operator. Other configurations of the data storage location may also be employed without departing from the scope of the present disclosure.

The data storage location may store a wide variety of data and information. In the embodiment of FIG. 13, the data storage location (in the form of a database 112) stores one or more subject data entries 120, with each subject data entry 120 corresponding to a subject (i.e., a donor or patient) upon which a medical procedure is to be performed using the system 110. The database 112 is pre-programmed with the subject data entry 120 for a particular subject at a time prior to the system 110 carrying out a medical procedure on that particular subject. Each subject data entry 120 includes subject-specific information 122, such as name, weight, sex, age, birth date, address, unique password, fingerprint, facial or retinal data, and/or answer(s) to security questions. The subject-specific information 122 corresponds to the identity of the subject and is compared to identity input 126 which is entered into the system by the subject, as will be described in greater detail below.

In addition to the subject-specific information 122, each subject data entry 120 may include one or more parameters 124 or such parameter(s) may be calculated or determined by the controller 118 based on the medical procedure and/or a combination of the procedure and subject-specific information 122. The nature of the parameter 124 may vary depending on the nature of the medical procedure to be performed. Also, the parameter 124 may relate to or be derived based on the sex of the subject, the weight of the subject, the acceptable rate at which fluid may be drawn from and/or returned to the subject (e.g., a citrate infusion rate), etc.

The user interface 114 includes a display for receiving commands and information from an operator or subject and displaying instructions for the operator or subject to perform. The display may be variously provided, such as in the form of a touch screen or, alternatively, a screen with an associated device which allows an operator or subject to interact with the user interface 114 (e.g., a keypad or keyboard). The user interface 114 also includes an input device for receiving an identity input 126 from the subject, which corresponds to the identity of the subject. As will be described in greater detail below, there are a variety of ways in which a subject may identify him- or herself, so the input device may be variously configured. In some embodiments, the display serves as an input device, while in other embodiments, the input device is separate from the display.

The principles of the present disclosure may be employed in a wide variety of devices and in a wide variety of procedures. Accordingly, the treatment device 116, which actually performs (at least part of) a medical procedure on the subject, may be variously configured. In one embodiment, the treatment device 116 may be an apheresis system, for example, a centrifuge system configured to draw blood from a subject, separate it into its constituents, and return at least one of the components to the subject. Exemplary centrifuge systems include those currently marketed as the ALYX® and AMICUS® systems by Fenwal, Inc. of Lake Zurich, Ill., as described in greater detail in U.S. Pat. Nos. 6,325,775 and 5,868,696, respectively, which are hereby incorporated herein by reference. Other treatment devices may also be employed without departing from the scope of the present disclosure, including (without limitation) dialysis systems, parenteral nutrition systems and others.

The controller 118 is associated with or in communication with the database 112, the user interface 114, and the treatment device 116. The controller 118 may be configured or programmed with a plurality of functions or procedures, and has various functions, including (but not limited to) receiving data from the various other components of the system 110, issuing commands to the various other components of the system 110, and monitoring the performance of the various other components of the system 110. In one embodiment, the controller 118 is configured to compare the identity input 126 which is provided by the subject to the subject data entries 120 stored in the database 112. If the identity input 126 corresponds to the subject-specific information 122 stored in one of the subject data entries 120 (i.e., if the system 110 "recognizes" the subject), the controller 118 will command the treatment device 116 to perform a medical procedure with respect to the subject. This may include determining or accessing the parameter(s) 124 associated with that particular subject data entry 120 (if provided) and sending the parameter(s) 124 to the treatment device 116 for use in performing the medical procedure.

If the identity input 126 does not correspond to the subject-specific information 122 stored in any of the subject data entries 120, the controller 118 may initiate any of a number of responses. In one embodiment, the controller 118 generates an error signal that prevents the performance of the medical procedure with respect to the subject. The error signal may trigger audible and/or visual alarms and alerts, including commanding the user interface 114 to show an error message (e.g. "Unable to confirm individual") on the display. In another embodiment, the controller 118 optionally commands the treatment device 116 to perform the procedure on the subject using default operational parameters instead of parameters uniquely suited to the subject.

Figure 14:
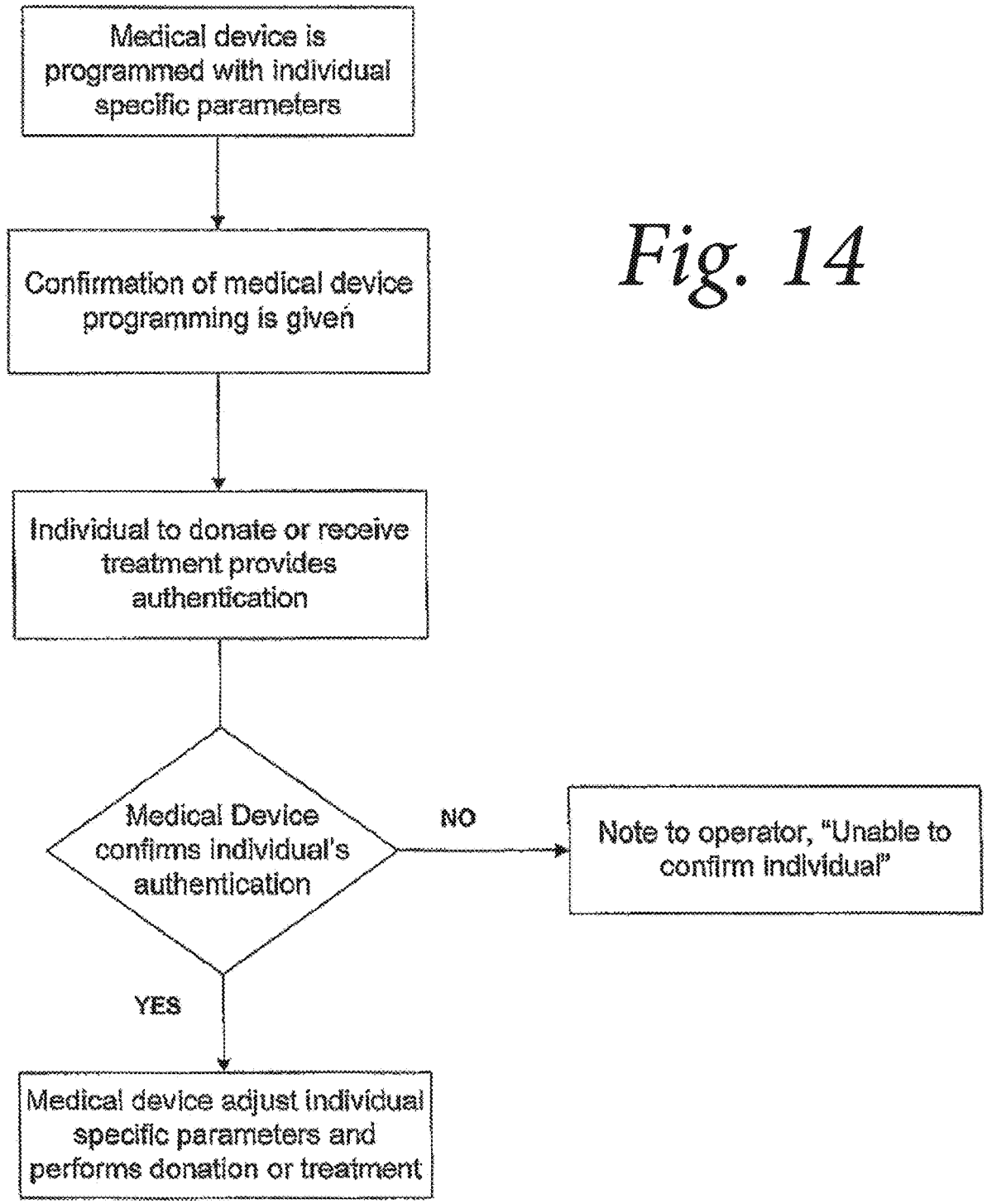
FIG. 14 is a flowchart which shows the process undertaken by the medical device of FIG. 13 when receiving identity information from a subject and then performing a medical procedure with respect to the subject.

FIG. 14 illustrates an exemplary manner of using a system 110 according to the present disclosure. Prior to a medical procedure being performed on the subject, a subject data entry 120 is pre-programmed into the database 112 for the subject. This may be done remotely or by using the user interface 114. A medical personnel is prompted to enter a variety of information, including at least the subject-specific information 122 which will be used to identify the subject. The medical personnel may also be prompted to enter one or more parameters 124 to be used when performing the medical procedure with respect to the subject. Depending on the nature of the identity input 126, the nature of the subject-specific information 122 and, hence, the manner and form in which it is entered into the database 112 may vary. For example, the information may be retrieved from another database, such as a central or remote database by direct interrogation and download, or in response to subject or medical personnel input. The remote database may be a donor management system, as described herein with reference to the embodiments of FIGS. 1-12. Information or parameters may be retrieved from the remote database for use in a plasma collection process as described with reference to FIGS. 1-12 herein. Further, the nature of the parameter(s) 124 may depend on the nature of the medical procedure to be performed with respect to the subject. When the subject-specific information 122 and optionally parameter(s) 124 (if provided) have been entered into the system 110, the medical personnel may confirm the data entered, thereby generating a subject data entry 20 which is stored in the database 112 and is unique to the subject.

At some later time, the subject is brought into the vicinity or proximity of the system 110 or an operable portion of the system 110. The subject may be connected to the treatment device 116 upon being brought into the vicinity of the system 110 or may be connected to the treatment device 116 at a later time (e.g., after the system 110 has confirmed the identity of the subject). While in the vicinity of the system 110, the subject attempts to identify him- or herself to the system 110 by providing an identity input 126 via the input device of the user interface 114. The identity of a subject may be expressed in any of a number of ways, so the system 110 may include one or more different input devices for receiving the identity input 126.

In one embodiment, the identity input 126 may take the form of biometric data, in which case the input device of the user interface 114 is provided as a biometric scanner or reader. For example, the input device may be provided as a fingerprint reader to receive and analyze the fingerprint of a subject. In another embodiment, the input device is provided as a retina scanner to view and analyze the retina of a subject. In yet another embodiment, the input device includes face recognition software to view and analyze the face of a subject. In another embodiment, the input device is provided as a heart rate monitor to consider the heart rhythm of a subject. In yet another embodiment, the input device includes a microphone or comparable audio device to receive and analyze the voice of a subject. In another embodiment, the input device is configured to receive a blood sample from a subject and analyze the DNA of the subject. Other biometric identifiers may also (or additionally) be provided by a subject to express his or her identity.

In another embodiment, the subject is provided with a unique subject identification card, badge, or removable storage device which is analyzed by the input device to attempt to identify the subject to the system 110. For example, the input device may comprise a bar code reader, with the subject being provided with a subject identification card having personal information encoded into a bar code which can be read by the input device. In another example, the subject may have a subject identification card encoded with personal information and having a built-in radio-frequency identification ("RFID") circuit. The input device comprises an RFD reader which is capable of reading the personal information on the card for subsequent analysis by the controller 118. The card may serve as a data storage location, as described above, being further encoded with one or more of the subject's unique operational parameters 124, rather than pre-programming the parameter(s) 124 into the database 112 or deriving/calculating them by the controller 118. In this case, the identity input 126 and the parameter(s) 124, if any, will be read by the input device and, if the identity input 126 corresponds to the subject-specific information 122 in one or more of the subject data entries 120, the controller 118 will send the parameters) 124 from the card to the treatment device 116. Furthermore, the card may be encoded with a multiple-treatment regimen, with the result of each treatment being tracked by the system 110 over time.

In one or more embodiments, the controller 118 may be programmed to require certain one or more of the subject-specific information 122 in the subject data entries 120 to correspond to the identity input 126. For example, the system 110 may require a combination of correct subject-specific information 122 before proceeding with the medical procedure. Specifically, the system 110 may require two or more subject-specific information 122 to be consistent with the identity input 126 and/or with each other. As non-limiting examples, the system 110 may require consistency among a name and sex; a name and password; a name and fingerprint and medical condition; a fingerprint and facial recognition; or such other combination as may be selected.

In yet another embodiment, the input device of the user interface 114 is programmed to recognize and read authentication software running on an electronic device, such as a mobile phone or laptop computer.

In another embodiment, the user interface 114 is programmed to receive a personal identification number, code, or password from the subject. If the display of the user interface 114 is a touch screen, the personal identification number may be directly entered using the display (thereby allowing the display to serve as the input device). Alternatively, an input device comprising a keypad or keyboard may be provided to allow the subject to enter the personal identification number.

When the subject has provided the identity input 126 to the system 110, the controller 118 compares the identity input 126 to the subject data entries 120 stored in the database 112. As described above, if the identity input 126 corresponds to the subject-specific information 122 stored in one or more of the subject data entries 120, as required by the system 110 (represented in FIG. 14 as a "YES" response to the "if-then" diamond containing the words "Medical Device confirms individual's authentication"), the system 110 has successfully identified the subject. The controller 118 will then command the treatment device 116 to perform a medical procedure (e.g., plasma collection, red blood cell collection, etc.) with respect to the subject, which may include the controller 118 computing, retrieving, or accessing the parameter(s) 124 associated with that particular subject data entry 120 and sending it/them to the treatment device 116 for use in performing the medical procedure.

If the controller 118 is unable to match the identity input 126 to the subject-specific information 122 stored in any of the subject data entries 120 (represented in FIG. 14 as a "NO" response to the "if-then" diamond containing the words "Medical Device confirms individual's authentication"), the system 110 has failed to identify the subject. In the embodiment of FIG. 14, the controller 118 responds by disabling or declining to proceed with the medical procedure and may generate a signal that prevents the performance of the medical procedure with respect to the subject. The subject may then be given one or more additional opportunities to express his or her identity using the same or a different identity input 126. As described above, different responses to a failed identification may also be initiated without departing from the scope of the present disclosure.

Figure 15:
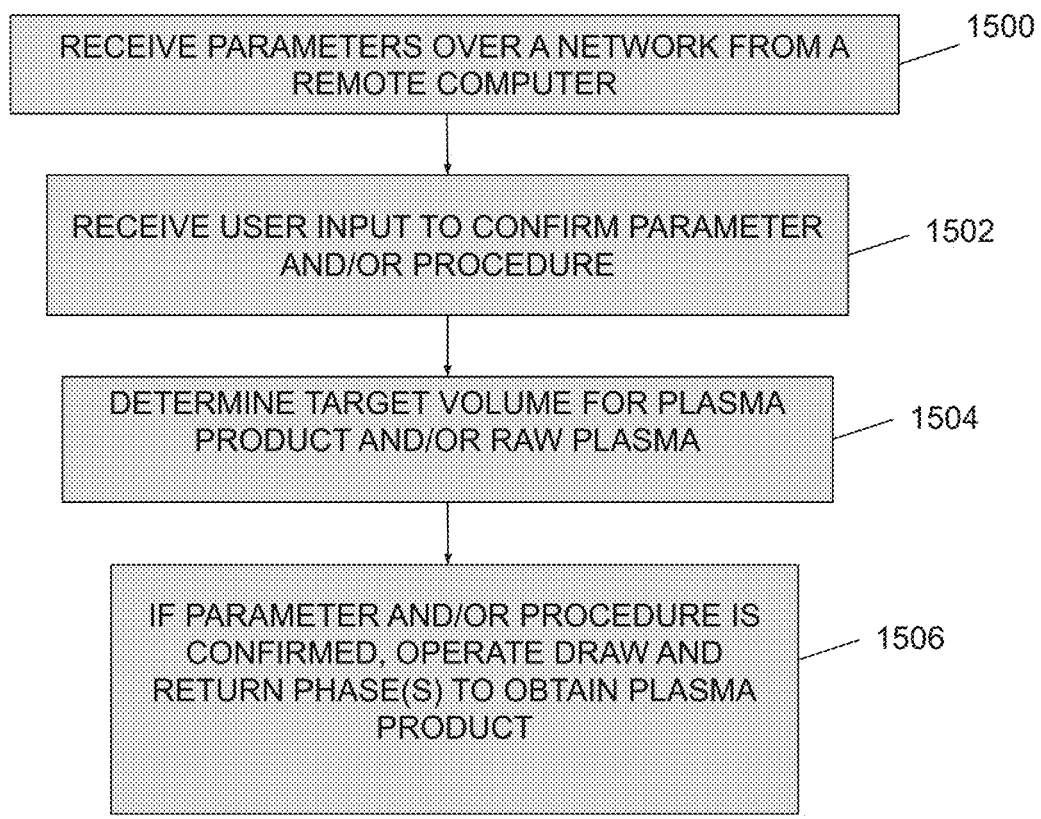
FIG. 15 is a flowchart of a method for collection plasma, according to another illustrative embodiment.

Referring now to FIG. 15, a system and method for collecting plasma will be described, according to an illustrative embodiment. This embodiment may be implemented with one or more components or functions described above, such as the venipuncture needle, blood separator, donor line, anticoagulant line, pumps, touchscreen and controller, etc. At a block 1500, a controller is programmed to receive parameters over a network from a remote computer. The parameters may comprise one or more of donor parameters or operating parameters. The parameters may comprise one or more of sex, age, height, weight, pregnancy data, hematocrit, subject-specific information, name, birth date, home address, unique password, fingerprint, facial or retinal data, answer(s) to security questions, citrate infusion rate, image of donor, target volume for plasma product (e.g., plasma plus anticoagulant), target volume for raw plasma, anticoagulant ratio, total blood volume of donor, total plasma volume of donor, parameters relating to total blood volume calculations described herein, and/or other parameters. In some embodiments, the remote computer performs calculations described herein based on one or more of the parameters. In some embodiments, the controller performs calculations described herein based on one or more of the parameters.

At a block 1502, the controller may be configured to receive a user input to confirm the donor based at least in part on at least one of the parameters. For example, controller may display a parameter which identifies the donor (e.g., donor identity code or number, name, a birthdate, a social security number, an image, etc.) on a touch screen or other display and may be configured to receive a confirmation input from an operator/user. The user may confirm by pressing a button displayed on the teach screen labeled "confirm," by voice command to a microphone coupled to the controller, by use of a keyboard, or by other user input devices. The operator may first confirm with the donor by speaking to the donor, looking at the donor to confirm an image, etc., and then the operator may provide the input to the controller through a suitable user input device, such as the touch screen.

At a block 1504, controller may be configured to determine a target volume for plasma product and/or raw plasma based at least in part on at least one of the parameters. As described hereinabove, the determination may be made by receiving the target volume for plasma product and/or raw plasma from a remote computer, by calculating the target volume for plasma product and/or raw plasma locally to the blood collection device, by receiving input data from an operator from a user input device, or by other methods of determining. Calculations done on the remote computer or locally on at the controller may be based on the simplified plasma volume nomogram described hereinabove, by first calculating total blood volume of the donor and/or total plasma volume as described hereinabove, or using any other calculations described herein.

At a block 1506, provided the donor is confirmed by the operator, the controller may be configured to control the system to operate one or more (at least two, at least three, at least four, etc.) draw and return phases to withdraw whole blood from a donor and separate the whole blood into the plasma product and the second blood component and to return the second blood component to the donor.

The parameters received by the controller from the remote computer may comprise an image of the donor, the controller programmed to display the image on the touchscreen and to receive the user input from the touch screen to confirm the donor. The parameters received by the controller from the remote computer may comprise a donor identifier, wherein the system further comprises a scanner configured to scan a code associated with a donor. The scanner may be a barcode scanner, camera, or other scanning device. The controller and/or scanner may be configured to receive scanned data from the scanner from a wristband of the donor.

The parameters received by the controller from the remote computer may comprise at least one data unique to or characteristic of the donor, such as a social security number, a birth date, an image, etc. The controller may be configured to display the at least one data unique or characteristic of the donor and prompt the user to confirm the donor is associated with the data unique to or characteristic of the donor.

In one embodiment, the remote computer is configured to calculate the target volume for plasma product and/or raw plasma based on at least two of weight, height, hematocrit and gender of the donor.

In another embodiment, a weight scale may be used to obtain donor weight. The weight scale may be coupled to one of the remote computer and the controller. At least one of the remote computer and the controller may be configured to receive the weight of the donor from the weight scale. The target volume for plasma product and/or raw plasma may be determined based at least in part on the weight from the weight scale.

In one embodiment, the controller or remote computer may be configured with a camera to acquire an image of the donor. The controller or remote computer may comprise a processing circuit configured to use image processing techniques to determine a body mass index (BMI) of the donor. The BMI can be a parameter used in the calculation of total blood volume. The controller or remote computer may be programmed to compare the calculated BMI to a weight and/or height entered by an operator or obtained from a weight scale. If the weight deviates from that expected by the calculated BMI, the controller or remote computer may be configured to generate a message for display indicating the patient should be re-measured, in weight and/or height.

In another embodiment, parameters relating to the donor, such as height, weight, etc. may be categorized in memory as constant factors (e.g., sex) or varying factors (e.g., weight, hematocrit, height). The controller or remote computer may be configured to require a re-measure or re-entry of varying factors at each donation, whereas constant factors need not be re-entered and may even be grayed-out in a user input screen.

Referring now to FIG. 16, a system and method of collecting plasma (or other blood components) from a donor using a handheld computer will be described. A remote computer 1600 may be one or more computing devices configured to function as a donor management system for managing donor data. Computer 1600 may also receive and store donor intake data, such as weight, height, sex, hematocrit, blood pressure, dates of previous donations, and answers to donor qualification questions for determining if a donor is qualified to make a donation. The remote computer 1600 may be disposed remotely from the blood processing device 1604, such as in another room of a blood collection facility, an off-site location, etc. A handheld computer 1602 may comprise a housing configured to be held in a hand during use, such as a smartphone, personal digital assistant, mobile telephone, or other handheld device. Blood processing device 1604 may comprise a plasmapheresis device or other apheresis device which may be designed to collect, process, and/or treat one or more different blood components in different modes. Each of devices 1600, 1602 and 1604 may be configured to communicate with one or both other devices over a network interface circuit configured for wired and/or wireless communication over networks, such as a local area network, a wide area network, an 802.11x or Wi-Fi network, etc.

In one aspect, handheld device 1602 may be configured to receive parameters from remote computer 1600, such as a donor identifier (e.g., name, social security number, digital image, donor code, birthdate, or other data which is unique to or characteristic of a donor, etc.), donor height, weight, hematocrit, sex, etc., target plasma product and/or raw plasma to collect (as calculated by remote computer 1600), or other parameters. One or more of the parameters may be displayed on a display of handheld computer 1602 (e.g., a display having input and/or output capability, a touchscreen display having input capability, etc.) and an operator may be prompted on the display to confirm one or more of the parameters. For example, an operator may see an image or name of a donor on the screen, as well as a prompt (e.g., text) asking the operator to confirm that the donor presenting for the donation is the same as that identified on the screen. A touchscreen button may be provided for the operator to confirm the donor or other parameters or procedure.

Based on the confirmation by the operator (e.g., upon confirming, after confirming, or after confirming followed by additional steps), handheld computer 1602 may be configured to transmit or provide one or more parameters to blood processing device 1604. For example, parameters may be downloaded wirelessly to blood processing device 1604. Alternatively, parameters may be displayed on the display of handheld computer 1602 so that the operator can see them and manually enter them into blood processing device 1606 using an input device, such as a touch screen.

In another embodiment, parameters may be transmitted wirelessly from remote computer 1600 directly to blood processing device 1604, wherein blood processing device 1604 awaits use, loading or beginning a blood processing procedure based on the parameters until such time as confirmation occurs on handheld computer 1602 (or directly on blood processing device 1604, as described in other embodiments disclosed herein). In one example, run parameters (e.g., target plasma product and/or target raw plasma to collect, components of blood to collect, etc.) may be transmitted to the apheresis device at the same time as donor identification data is transmitted to handheld device 1602, and the operator can start the procedure on blood processing device 1604 as soon as the donor identification is confirmed, and the donor identification may be linked to the device parameters.

Parameters received at handheld computer 1602 from remote computer 1600 or from a user interface of handheld computer 1602 may be transmitted to blood processing system 1604 in using any of a number of technologies, such as wireless transmission, memory card, etc. In one embodiment, blood processing device 1604 comprises a scanning device, such as a camera, bar code reader, etc., configured to receive an image encoding parameters from a display of handheld computer 1602, from a paper, or from another source.

Remote computer 1600 may be configured to receive donor parameters, such as weight, height, sex, hematocrit, age, etc. and to calculate a target plasma product (plasma product plus anticoagulant) and/or target raw plasma based on these and/or other parameters, such as a predetermined anticoagulant ratio. Donor parameters may be received from an operator input device, from a Blood Establishment Computer Software system (BECS), or from other sources. Remote computer 1600 may be configured to transmit the target plasma produce and/or target raw plasma to handheld computer 1602 and/or blood processing system 1604.

Some donor parameters may be fixed, such as donor sex, while other donor parameters may be variable, such as weight and height. Some donor parameters may be more variable than others, for example, weight may be more variable than height. The systems described herein (e.g., remote computer 1600, handheld computer 1602, and/or donor processing system 1604) may be configured to store donor parameters with different fixed or variable characteristic identifiers, wherein the systems may be configured to have different requirements of the donor parameters before calculations and/or operations may be performed using those donor parameters. For example, the systems may be configured to calculate target plasma product and/or target raw plasma based on total body volume. Calculations for targets, total body volume, and/or total plasma volume may be made based on at least one parameters which is existing data to be retrieved from a database and at least one or at least two additional parameters which are currently obtained, measured data at or within a predetermined period of time before the donation procedure. In one example, donor height is existing data from the database while weight and hematocrit are measured and recorded on the same day as the apheresis procedure. In another example, the system may be configured to use height measured and recorded at least a predetermined time period (e.g., one day, three days, etc.) before a donation. The system may be configured to receive the height directly through a user portal to the system, for example in a self-report scenario. The system may be configured to receive the height from an identification document issued by a different entity (e.g., a primary care doctor, another donation facility, etc.) and recorded into the database at least three days before the procedure. Various donor parameters may be required to be fixed or variable in different parameters by the programming of the system.

In one embodiment, a method of collecting plasma from a donor comprises receiving parameters for a plasma collection procedure over a network from a remote computer at a controller local to a plasma collection device, the plasma collection device having a touch screen user input device. The method comprises receiving a user input at the touch screen to confirm at least one of the parameters and/or the procedure. The method comprises determining a target volume for plasma product and/or raw plasma based at least in part on at least one of the parameters received over the network from the remote computer. The method comprises, in response to confirming the at least one of the parameters and/or the procedure, controlling the plasma collection device to draw whole blood from the donor, combining anticoagulant with the whole blood, separating the whole blood into a plasma product and a second blood component comprising red blood cells, sending the plasma product to a plasma product collection container, and returning the second blood component to the donor.

The target volume for plasma product and/or raw plasma may be calculated at the remote computer, wherein determining the target volume for plasma product and/or raw plasma comprises receiving the target volume for plasma product and/or raw plasma from the remote computer at the controller.

The at least one of the parameters may be a donor identifier, wherein, in response to confirming the donor identifier, the plasma collection device is controlled to perform the plasma collection procedure according to the parameters.

The controller may be configured to receive the user input via the touchscreen to confirm the plasma collection procedure.

The controller may be configured to receive the parameters, store the parameters in a memory as a configured procedure, display an indication of the configured procedure via the touch screen, and receive the user input via the touch screen to confirm the configured procedure.

It will be understood that the embodiments described are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above-description but is set forth in the following claims.

The invention claimed is:

1. A system for collecting plasma, comprising:
a venipuncture needle configured to draw whole blood from a donor;
a blood separator configured to separate whole blood into a plasma product and a second blood component comprising red blood cells, the blood separator having a plasma output port coupled to a plasma line configured to send the plasma product to a plasma product collection container;
a donor line fluidly coupled to the venipuncture needle configured to introduce the whole blood from the donor to the separator, flow through the donor line being controlled by a first pump;
an anticoagulant line coupled to an anticoagulant source, the anticoagulant line configured to combine anticoagulant with the whole blood from the donor, flow through the anticoagulant line being controlled by a second pump,
a touchscreen configured to receive input from an operator; and
a controller configured to control operation of the system, the controller configured to receive parameters for a plasma collection procedure over a network from a remote computer, the remote computer comprising a donor management system by which a donor is screened prior to a donation and donor records are managed, to receive a user input via the touchscreen to confirm at least one of the parameters and/or the procedure, to determine a target volume for plasma product and/or raw plasma which is based at least in part on at least one of the parameters received over the network from the remote computer and, in response to confirming the at least one of the parameters and/or the procedure, to control the system to operate at least three draw and return phases to withdraw whole blood from a donor and separate the whole blood into the plasma product and the second blood component and to return the second blood component to the donor.

2. The system of claim 1, wherein the parameters comprise an image of the donor, the controller configured to display the image on the touchscreen and to receive the user input from the touch screen to confirm the donor.

3. The system of claim 1, wherein the parameters comprise a donor identifier, wherein the system further comprises a scanner configured to scan a code associated with a donor.

4. The system of claim 3, wherein the scanner is configured to scan the code from a wristband worn by the donor.

5. The system of claim 3, wherein the parameters comprise at least one data unique to or characteristic of the donor, wherein the controller is configured to display the at least one data unique to the donor and prompt the user to confirm the donor is associated with the data unique to the donor.

6. The system of claim 5, wherein the at least one data unique to or characteristic of the donor is a social security number or a birth date.

7. The system of claim 1, wherein the controller is configured to determine the target volume for plasma product and/or raw plasma by receiving the target volume for plasma product and/or raw plasma as one of the parameters from the remote computer.

8. The system of claim 7, further comprising the remote computer, wherein the remote computer is configured to calculate the target volume for plasma product and/or raw plasma based on at least two of weight, height, hematocrit and gender of the donor.

9. The system of claim 1, further comprising the remote computer and a weight scale coupled to one of the remote computer and the controller, wherein at least one of the remote computer and the controller is configured to receive the weight of the donor from the weight scale, wherein the target volume for plasma product and/or raw plasma is determined based at least in part on the weight from the weight scale.

10. The system of claim 1, wherein the controller determines the target volume for plasma product and/or raw plasma by calculating the target volume for plasma product and/or raw plasma and wherein the controller is local to and coupled to the blood separator.

11. The system of claim 1, wherein the donor parameters received electronically from the remote computer comprise a donor weight, wherein the controller is configured to determine the target volume for plasma product and/or raw plasma based at least in part on the donor weight.

12. The system of claim 11, wherein the donor parameters received electronically from the remote computer comprise a donor hematocrit, wherein the controller is configured to determine the target volume for plasma product and/or raw plasma based at least in part on the donor hematocrit.

13. The system of claim 12, wherein the controller is configured to determine a target volume for plasma product based on the donor's total blood volume and the donor's plasma volume.

14. The system of claim 13, wherein the controller is configured to determine the donor's total blood volume based on the weight and height of the donor.

15. The system of claim 14, wherein the controller is configured to determine the donor's total blood volume before whole blood is withdrawn from the donor during a donation.

16. The system of claim 15, wherein the controller is configured to determine the target volume for plasma product comprising raw plasma and anticoagulant, wherein the target volume for plasma product is determined prior to withdrawing the whole blood from the donor based at least in part on an anticoagulant ratio, the donor's weight and the donor's hematocrit.

17. The system of claim 1, further comprising a reservoir separate from the blood separator for receiving concentrated red blood cells.

18. The system of claim 1, wherein the controller is further configured to, after controlling the system to operate a draw phase and a return phase, establish an updated value of hematocrit of the donor and a new target volume for plasma product and/or raw plasma based on the updated value of hematocrit, and to control the system to operate a subsequent draw and return cycle, whereby the donor's changing hematocrit is taken into account in calculating the new target volume for plasma product and/or raw plasma.

19. The system of claim 1, wherein the parameters received by the controller comprise at least a donor's weight, height, sex and hematocrit, the controller to determine the target volume for plasma product and/or raw plasma based at least in part on the weight, height, sex and hematocrit and to control the system to operate the draw and return phases until the target volume is reached.

20. The system of claim 1, further comprising the remote computer, wherein the remote computer is configured to calculate the target volume based on at least a donor's weight, height, sex and hematocrit, wherein the controller is configured to determine the target volume by receiving the target volume from the remote computer.

21. The system of claim 1, wherein the controller is configured to receive at least a donor's weight, height and hematocrit and to determine the target volume for plasma product comprising raw plasma and anticoagulant, wherein the target volume for plasma product is determined prior to withdrawing the whole blood from the donor based at least in part on an anticoagulant ratio, the donor's weight, height and the donor's hematocrit, the controller configured to then control the system to operate the draw and return cycles.

22. The system of claim 21, wherein the controller is configured to determine the target volume for plasma product based on the donor's total blood volume and the donor's plasma volume.

* * * * *